US011807843B2

(12) United States Patent
Yamazaki et al.

(10) Patent No.: US 11,807,843 B2
(45) Date of Patent: Nov. 7, 2023

(54) CELL CULTURE DEVICE AND METHOD OF USING THE SAME

(71) Applicant: TOYODA GOSEI CO., LTD., Kiyosu (JP)

(72) Inventors: Masateru Yamazaki, Kiyosu (JP); Yasuhiko Shinoda, Kiyosu (JP); Seitaro Taki, Kiyosu (JP); Shinji Oguchi, Kiyosu (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 820 days.

(21) Appl. No.: 16/810,018

(22) Filed: Mar. 5, 2020

(65) Prior Publication Data

US 2020/0308522 A1   Oct. 1, 2020

(30) Foreign Application Priority Data

Mar. 28, 2019 (JP) ................................. 2019-065126
Mar. 28, 2019 (JP) ................................. 2019-065127

(51) Int. Cl.
*C12M 3/00* (2006.01)
*C12M 1/12* (2006.01)

(52) U.S. Cl.
CPC ............ *C12M 23/48* (2013.01); *C12M 23/44* (2013.01); *C12M 25/02* (2013.01)

(58) Field of Classification Search
CPC ...... C12M 23/06; C12M 23/44; C12M 23/48; C12M 25/02; C12M 35/08
See application file for complete search history.

(56) References Cited

U.S. PATENT DOCUMENTS

| 2012/0183987 A1* | 7/2012 | Gevaert ............. G01N 33/5011 435/325 |
| 2017/0037353 A1 | 2/2017 | Taki et al. |
| 2017/0129690 A1 | 5/2017 | Sugawara et al. |

FOREIGN PATENT DOCUMENTS

| JP | 2006-006136 A | 1/2006 |
| JP | 2007-167002 A | 7/2007 |

(Continued)

OTHER PUBLICATIONS

Japanese Office Action dated Apr. 5, 2022 issued in corresponding JP Application No. 2019-065126 (and English translation attached).

(Continued)

*Primary Examiner* — Lydia Edwards
(74) *Attorney, Agent, or Firm* — POSZ LAW GROUP, PLC

(57) ABSTRACT

A cell culture device includes a holding member including a main body cylindrical portion extending in a cylindrical shape in an axial direction and a holding portion provided at an axially intermediate portion of the main body cylindrical portion and holding a culture membrane; and a first cylindrical member detachably mounted on one axial side with respect to the holding member, extending in a cylindrical shape in the axial direction, and protruding from one axial end of the holding member toward the one axial side when being mounted to the holding member. Also included is a second cylindrical member detachably mounted on another axial side with respect to the holding member, extending in a cylindrical shape in the axial direction, and protruding from another axial end of the holding member toward the other axial side when being mounted to the holding member.

7 Claims, 12 Drawing Sheets

(56) References Cited

FOREIGN PATENT DOCUMENTS

JP          2017-029092  A      2/2017
WO          2015/152415  A1    10/2015

OTHER PUBLICATIONS

Japanese Office Action dated Apr. 5, 2022 issued in corresponding JP Application No. 2019-065127 ( and English translation attached).

* cited by examiner

CELL CULTURE DEVICE AND METHOD OF USING THE SAME

CROSS-REFERENCE TO RELATED APPLICATIONS

This application is based upon and claims the benefit of priority from prior Japanese patent application No. 2019-065126, filed on Mar. 28, 2019 and Japanese patent application No. 2019-065127, filed on Mar. 28, 2019, the entire contents of which are incorporated herein by reference.

TECHNICAL FIELD

The present invention relates to a cell culture device used for culturing cells and a method of using the same.

BACKGROUND ART

There is available a cell culture device for culturing cells on both surfaces of a culture membrane (for example, Patent Literature 1). The cell culture device described in Patent Literature 1 includes a culture membrane, an outer cylinder, and an inner cylinder. The outer cylinder includes a main body cylindrical portion extending in a cylindrical shape in an axial direction. The main body cylindrical portion of the outer cylinder is provided with a slit extending in the axial direction. The outer cylinder is elastically deformable in a radial direction due to the presence of the slit. The outer cylinder includes a holding portion holding the culture membrane provided at an axial intermediate portion of the main body cylindrical portion.

Two inner cylinders are provided and each extend in a cylindrical shape in the axial direction. The first inner cylinder includes a facing portion facing the holding portion of the outer cylinder. The first inner cylinder is inserted into the outer cylinder from one axial side of the outer cylinder and is arranged adjacent to the outer cylinder. In addition, the second inner cylinder is inserted into the outer cylinder from the other axial side of the outer cylinder and is arranged adjacent to the outer cylinder. In a state in which each inner cylinder is inserted and mounted into the outer cylinder, the outer cylinder is elastically deformed radially outward, so that the inner cylinder and the outer cylinder are in contact with each other in the radial direction, and the facing portion of the first inner cylinder and the holding portion of the outer cylinder face each other in the axial direction, so that the culture membrane is sandwiched and held.

Patent Literature 1: JP-A-2017-29092

In the cell culture device described above, the two inner cylinders are formed such that axial tip ends of the respective inner cylinders do not protrude axially outward from axial end surfaces of the outer cylinder when mounted to the outer cylinder, respectively. Further, the outer cylinder is formed in a relatively long axial length so that the two inner cylinders can be mounted at the same time, and a dimensional distance from a lower end of the outer cylinder in the axial direction to the culture membrane in the cell culture device is long. Therefore, in order to culture cells in the culture membrane, it is necessary to increase a volume of a well (culture vessel), and it is necessary to prepare a large amount of culture solution.

The present invention has been made in view of the above circumstances, and an object thereof is to provide a cell culture device capable of culturing cells on a culture membrane with a small amount of culture solution, and a method of using the same.

SUMMARY OF INVENTION

According to an aspect of the invention, there is provided a cell culture device comprising: a holding member including a main body cylindrical portion extending in a cylindrical shape in an axial direction and a holding portion provided at an axially intermediate portion of the main body cylindrical portion and holding a culture membrane; a first cylindrical member detachably mounted on one axial side with respect to the holding member, extending in a cylindrical shape in the axial direction, and protruding from one axial end of the holding member toward the one axial side when being mounted to the holding member; and a second cylindrical member detachably mounted on another axial side with respect to the holding member, extending in a cylindrical shape in the axial direction, and protruding from another axial end of the holding member toward the other axial side when being mounted to the holding member.

DESCRIPTION OF EMBODIMENTS

Hereinafter, specific embodiments of a cell culture device and a method of using the same according to the present invention will be described with reference to the drawings.

First Embodiment

Figure 1:
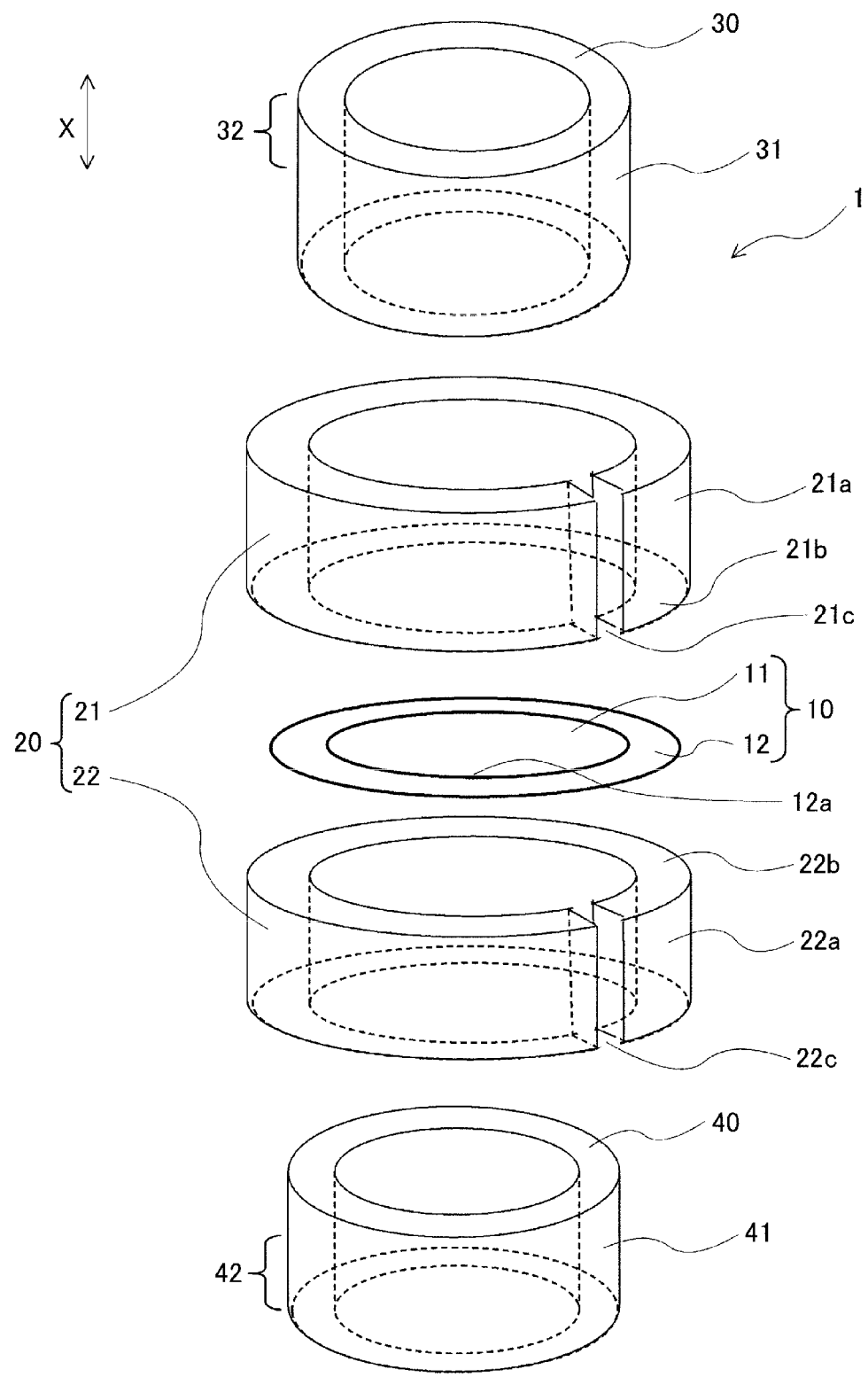
FIG. 1 is an exploded perspective view of a cell culture device according to a first embodiment.

A cell culture device 1 of a first embodiment is a device for culturing anchorage-dependent cells. The cell culture device 1 is capable of culturing two types of cells on both surfaces of a membrane. As shown in FIG. 1, the cell culture device 1 includes a culture membrane 10, a holding member 20, a first cylindrical member 30, and a second cylindrical member 40.

The culture membrane 10 is a sheet-like membrane on which cells are cultured. The culture membrane 10 includes a membrane body 11 and a support frame 12. The membrane body 11 is a membrane main body portion serving as a scaffold for cells when cells are cultured. The membrane body 11 is a porous membrane provided with pores on both surfaces thereof. The membrane body 11 is formed of a thermosetting resin such as polyurethane, silicone resin, phenol resin, epoxy resin, unsaturated polyester, or polyimide. A thickness of the membrane body 11 is, for example, 0.1 μm to 100 μm.

The support frame 12 is a base material which supports and reinforces the membrane body 11. The support frame 12 is an annular frame body having a circular hole 12a opened in a center portion thereof. The support frame 12 is joined and fixed to a peripheral edge of the membrane body 11. Incidentally, a shape of the support frame 12 may include at least an annular frame body portion, and may further include a protruding portion protruding radially outward from a part of the frame portion in a peripheral direction. The protruding portion has a function for facilitating handling when a person grips the culture membrane 10 with a jig such as a tweezer, for example. The support frame 12 is formed of a material harder than the membrane body 11. The material of the support frame 12 is, for example, a thermoplastic resin such as polyethylene, polypropylene, ABS resin, acrylic resin, and polyethylene terephthalate (PET), or a thermosetting elastomer such as silicone rubber. A thickness of the support frame 12 is, for example, 0.05 mm to 0.5 mm.

The holding member 20 is a member for holding the culture membrane 10. The holding member 20 is formed of a resin material, rubber, or the like. The holding member 20 includes two holding cylinders, that is, a first holding cylinder 21 and a second holding cylinder 22. The first holding cylinder 21 and the second holding cylinder 22 are arranged adjacent to each other in an axial direction X. The first holding cylinder 21 and the second holding cylinder 72 hold the culture membrane 10 in a state of being engaged with and fixed to each other. The culture membrane 10 held by the holding member 20 is exposed on both axial sides through axial openings of the first holding cylinder 21 and the second holding cylinder 22.

Figure 2:
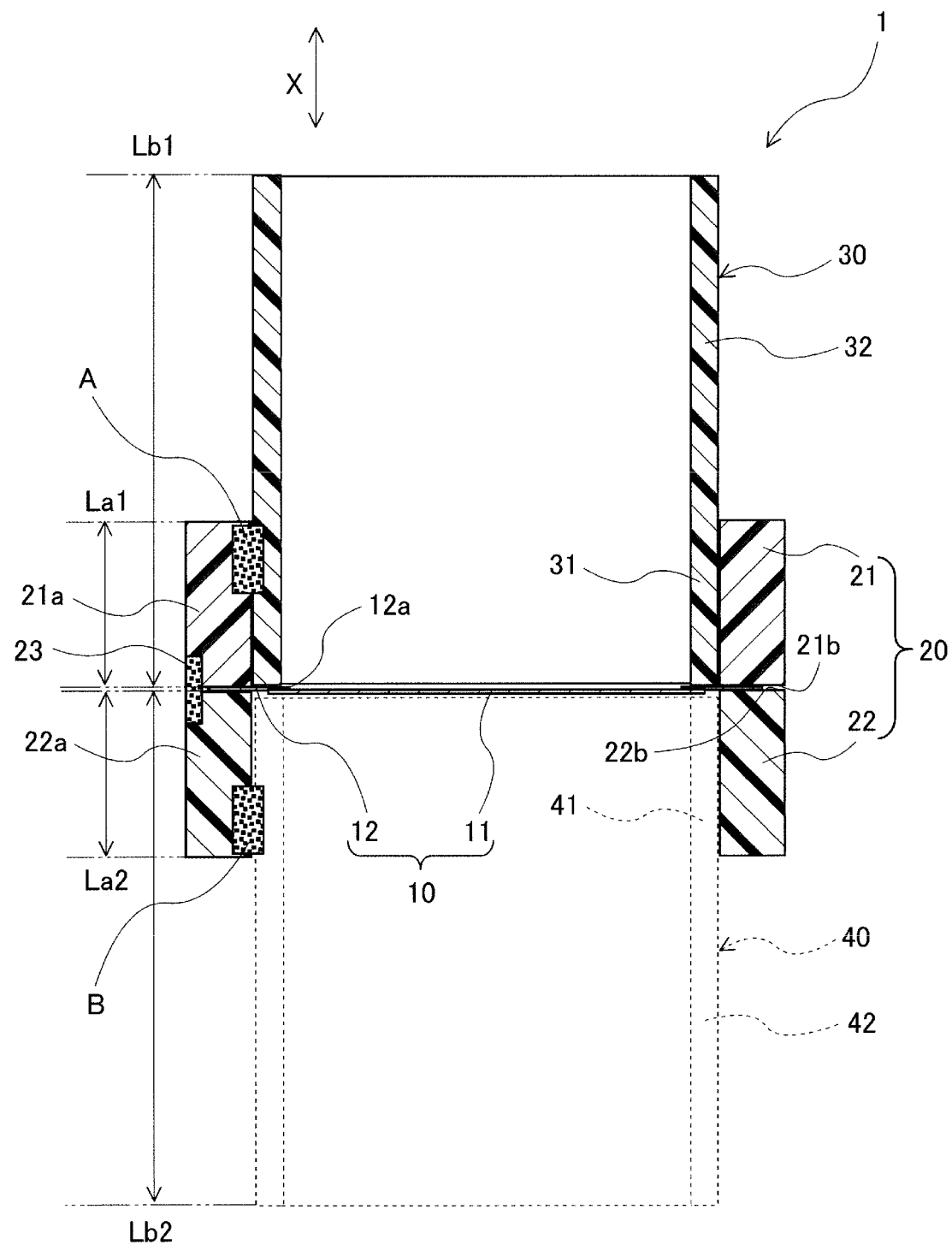
FIG. 2 is a sectional view of the cell culture device of the first embodiment.

The first holding cylinder 21 and the second holding cylinder 22 are members which are engageably attached to each other and have a structure 23 by which the first holding cylinder 21 and the second holding cylinder 22 are engaged with and fixed to each other as shown in FIG. 2. The engagement structure 23 is a locking structure which restricts relative movements between the first holding cylinder 21 and the second holding cylinder 22 in the axial direction X and radial direction by which the first holding cylinder 21 and the second holding cylinder 22 are separated from each other in an assembled state thereof. The engagement structure 23 is provided at two or more positions in a peripheral direction (for example, three to five positions) in the first holding cylinder 21 and the second holding cylinder 22. In addition, in a structure in which slits extending in the axial direction X are respectively provided in the holding cylinders 21 22, the engagement structure 23 is preferably provided at each of divided portions sandwiching the slit in the peripheral direction.

In a state in which the first holding cylinder 21 and the second holding cylinder 22 are engaged with and fixed to each other as described above, a distance in which axial end surfaces of the first holding cylinder 21 and the second holding cylinder 22 facing each other are separated in the axial direction X is set to be equal to or less than an axial thickness of the culture membrane 10 (specifically, the support frame 12 thereof) before assembling. Accordingly, the support frame 12 of the culture membrane 10 is sandwiched and fixed between the first holding cylinder 21 and the second holding cylinder 22. At this time, gaps between the support frame 12 and the first holding cylinder 21 and between the support frame 12 and the second holding cylinder 22 are sealed.

The engagement structure 23 between the first holding cylinder 21 and the second holding cylinder 22 may be, for example, an L-groove engagement structure including a radially recessed concave portion provided on an outer surface or an inner surface of one of the first holding cylinder 21 and the second holding cylinder 22, and a radially protruding convex portion provided on an inner surface or an outer surface of the other one. The concave portion may be, for example, a groove formed in an L shape when viewed from the radial direction.

The engagement structure 23 between the first holding cylinder 21 and the second holding cylinder 22 may be, for example, a snap-fit type engagement structure including an elastic deformation portion elastically deformable in the radial direction provided in one of the first holding cylinder 21 and the second holding cylinder 22, and a radially recessed groove portion provided on the other one. In the snap-fit type engagement structure, when the first holding cylinder 21 and the second holding cylinder 22 approach each other in the axial direction when be assembled, the first holding cylinder 21 and the second holding cylinder 22 are engaged with and fixed to each other by fitting a radially protruding claw portion provided an axial tip end portion of the elastic deformation portion into the groove portion and being hooked.

The first holding cylinder 21 includes a hollow first cylindrical portion 21a extending in a cylindrical shape in the axial direction X, a first holding portion 21b which holds the culture membrane 10, and a first side surface opening portion 21c which is provided so as to penetrate the first cylindrical portion 21a in the radial direction. The second holding cylinder 22 includes a hollow second cylindrical portion 22a extending in a cylindrical shape in the axial direction X, a second holding portion 22b which holds the culture membrane 10, and a second side surface opening portion 22c which is provided so as to penetrate the second cylindrical portion 22a in the radial direction.

The first cylindrical portion 21a and the second cylindrical portion 22a have respectively predetermined lengths La1, La2 in the axial direction X. Incidentally, the axial lengths of the first cylindrical portion 21a and the second cylindrical portion 22a may substantially coincide with each other. The first cylindrical portion 21a and the second cylindrical portion 22a constitute a main body cylindrical portion extending in a cylindrical shape in the axial direction X of the holding member 20.

Figure 3:
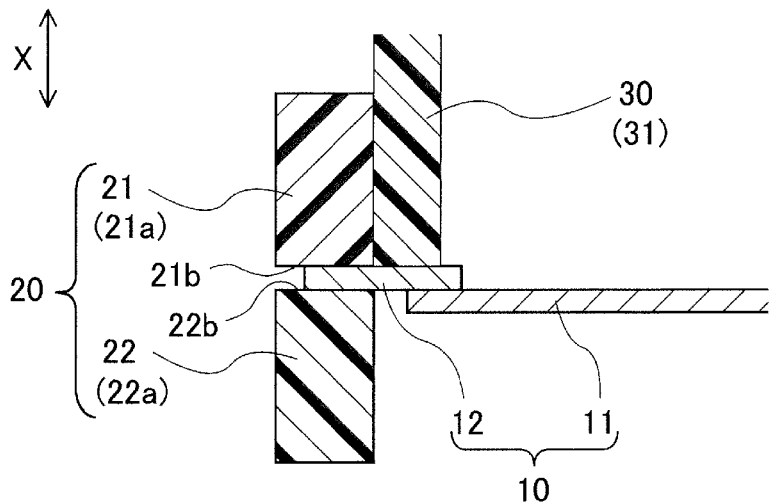
FIG. 3 is a sectional view for explaining a structure in which a culture membrane is held by a holding member in the cell culture device of the first embodiment.

The first cylindrical portion 21a and the second cylindrical portion 22a have respectively predetermined thicknesses in the radial direction. As shown in FIG. 3, outer diameters of the first cylindrical portion 21a and the second cylindrical portion 22a substantially coincide with each other, and inner diameters thereof substantially coincide with each other. An outer diameter of the culture membrane 10 (that is, an outer diameter of the support frame 12) exceeds the inner diameters of the first cylindrical portion 21a and the second cylindrical portion 22a. Incidentally, the outer diameter of the culture membrane 10 may be smaller than the outer diameters of the first cylindrical portion 21a and the second cylindrical portion 22a. The first holding cylinder 21 and the second holding cylinder 22 sandwich and hold the culture membrane 10 by engaging with each other in a state in which axial end surfaces of the first cylindrical portion 21a and the second cylindrical portion 22a facing in the axial direction X face each other.

The first holding portion 21b and the second holding portion 22b are the axial end surfaces of the first cylindrical portion 21a and the second cylindrical portion 22a which face each other, respectively. The axial end surfaces used as the first holding portion 21b and the second holding portion 22b are abutment portions which can abut against the support frame 12 of the culture membrane 10. The first holding portion 21b abuts against an axial end surface of the culture membrane 10 on one axial side. The second holding portion 22b abuts against the other axial end surface of the culture membrane 10 on the other axial side. Each of the first holding portion 21b and the second holding portion 22b is formed in an annular shape. The first holding portion 21b and the second holding portion 22b are each provided at an axial intermediate portion of the main body cylindrical portion of the entire holding member 20.

The first side surface opening portion 21c is a slit hole portion which is provided so as to penetrate a predetermined portion of the first cylindrical portion 21a in the radial direction, and communicates the inside of the first cylindrical portion 21a to the outside. The first side surface opening portion 21c is provided at one position in the peripheral direction. The predetermined portion in which the first side surface opening portion 21c is provided includes at least a portion on a lower side in the axial direction X than the culture membrane 10 held by the first holding portion 21b during cell culture in a state in which the first cylindrical portion 21a is positioned below the second cylindrical portion 22a, and is formed to extend from the first holding portion 21b to one axial side. The first side surface opening portion 21c extends over the entire axial direction of the first cylindrical portion 21a. The first side surface opening portion 21c has an air venting function of discharging air accumulated on a lower surface of the culture membrane 10 held by the first holding portion 21b to the outside.

The second side surface opening portion 22c is a slit hole portion which is provided so as to penetrate a predetermined portion of the second cylindrical portion 22a in the radial direction, and communicates the inside of the second cylindrical portion 22a to the outside. The second side surface opening portion 22c is provided at one position in the peripheral direction. The predetermined portion in which the second side surface opening portion 22c is provided includes at least a portion on the lower side in the axial direction X than the culture membrane 10 held by the second holding portion 22b during the cell culture in a state in which the second cylindrical portion 22a is positioned below the first cylindrical portion 21a, and is formed to extend from the second holding portion 22b to the other axial side. The second side surface opening portion 22c extends over the entire axial direction of the second cylindrical portion 22a. The second side surface opening portion 22c has an air venting function of discharging air accumulated on the lower surface of the culture membrane 10 held by the second holding portion 22b to the outside.

Each of the first cylindrical member 30 and the second cylindrical member 40 is a cylindrical member attached to the holding member 20. The first cylindrical member 30 and the second cylindrical member 40 are each formed of a resin material, rubber, or the like. The first cylindrical member 30 and the second cylindrical member 40 are selectively attached to the holding member 20 when cells are cultured on the culture membrane 10. That is, the first cylindrical member 30 is attached to the holding member 20 when first cells are seeded on one axial end surface of the culture membrane 10, while the second cylindrical member 40 is attached to the holding member 20 when second cells are seeded on the other axial end surface of the culture membrane 10.

The first cylindrical member 30 includes a hollow cylindrical portion 31 extending in a cylindrical shape in the axial direction X. The first cylindrical member 30 is mounted on one axial side of the holding member 20 (specifically, the first holding cylinder 21). The first cylindrical member 30 can be attached to/detached from the holding member 20 (specifically, the first holding cylinder 21). That is, the first cylindrical member 30 and the first holding cylinder 21 are engageably attached to each other. The first cylindrical member 30 and the first holding cylinder 21 have a structure A by which the first cylindrical member 30 and the first holding cylinder 21 are engaged with and fixed to each other, such as the engagement structure 23 of the first holding cylinder 21 and the second holding cylinder 22 of the holding member 20. The culture membrane 10 held by the holding member 20 is exposed to one axial side through an axial opening of the first cylindrical member 30.

The first cylindrical member 30 is formed so as to be insertable into the first holding cylinder 21 of the holding member 20. The first cylindrical member 30 is attached in a state of being inserted into the first cylindrical portion 21a of the first holding cylinder 21. The first cylindrical member 30 includes an outer diameter which coincides with the inner diameter of the first holding cylinder 21. The cylindrical portion 31 of the first cylindrical member 30 includes a first protruding portion 32 which protrudes from one axial end of the first holding cylinder 21 toward the one axial side in a state of being engaged with and fixed to the first holding cylinder 21.

Specifically, the first cylindrical member 30 is formed such that an axial end surface of the cylindrical portion 31 on an insertion side abuts against the one axial end surface of the culture membrane 10 sandwiched and fixed between the first holding cylinder 21 and the second holding cylinder 22, and an axial end surface of the cylindrical portion 31 on an opposite side to the insertion side is arranged at a position protruding toward one axial side from the one axial end of the first holding cylinder 21, in the state in which the first cylindrical member 30 is engaged with and fixed to the first holding cylinder 21. That is, a length Lb1 of the first cylindrical member 30 in the axial direction X is set to be larger than a length La1 of the first cylindrical portion 21a of the first holding cylinder 21 in the axial direction X.

The second cylindrical member 40 includes a hollow cylindrical portion 41 extending in a cylindrical shape in the axial direction X. The second cylindrical member 40 is mounted on the other axial side of the holding member 20 (specifically, the second holding cylinder 22). The second cylindrical member 40 can be attached to/detached from the holding member 20 (specifically, the second holding cylinder 22). That is, the second cylindrical member 40 and the second holding cylinder 22 are engageably attached to each other. The second cylindrical member 40 and the second holding cylinder 22 have a structure B by which the second cylindrical member 40 and the second holding cylinder 22 are engaged with and fixed to each other, such as the engagement structure 23 of the first holding cylinder 21 and the second holding cylinder 22 of the holding member 20. The culture membrane 10 held by the holding member 20 is exposed to the other axial side through an axial opening of the second cylindrical member 40.

The second cylindrical member 40 is formed so as to be insertable into the second holding cylinder 22 of the holding member 20. The second cylindrical member 40 is attached in a state of being inserted into the second cylindrical portion 22a of the second holding cylinder 22. The second cylindrical member 40 includes an outer diameter which coincides with the inner diameter of the second holding cylinder 22. The second cylindrical portion 41 of the second cylindrical member 40 includes a second protruding portion 42 which protrudes from the other axial end of the second holding cylinder 22 to the other axial side in a state of being engaged with and fixed to the second holding cylinder 22.

Specifically, the second cylindrical member 40 is formed such that an axial end surface of the cylindrical portion 41 on the insertion side abuts against the other axial end surface of the culture membrane 10 sandwiched and fixed between the first holding cylinder 21 and the second holding cylinder 22, and an axial end surface of the cylindrical portion 41 on an opposite side to the insertion side is arranged at a position protruding toward the other axial side from the other axial end of the second holding cylinder 22, in the state in which the second cylindrical member 40 is engaged with and fixed to the second holding cylinder 22. That is, a length Lb2 of the second cylindrical member 40 in the axial direction X is set to be larger than a length La2 of the second cylindrical portion 22a of the second holding cylinder 22 in the axial direction X.

Next, a method of assembling the cell culture device 1 and a method of using the same will be described with reference to FIGS. 4, 5, and 6.

The culture membrane 10, the holding member 20, the first cylindrical member 30, and the second cylindrical member 40, which are components of the cell culture device 1, are prepared. Incidentally, the culture membrane 10 and the holding member 20 may be those in which the culture membrane 10 is held by the first holding cylinder 21 and the second holding cylinder 22 of the holding member 20 being engaged with and fixed to each other.

The cell culture device 1 is assembled manually by a person using a jig such as a tweezer. In an assembling procedure, first, the first cylindrical member 30 is assembled to the holding member 20 holding the culture membrane 10. First, the first cylindrical member 30 is gripped by a jig in a state in which the holding member 20 is set such that an axial end portion side thereof from which the first cylindrical member 30 is inserted is positioned upward, then the first cylindrical member 30 is inserted into the holding member 20 by being moved from above in a direction approaching each other in the axial direction X, and thereafter, the holding member 20 and the first cylindrical member 30 are engaged with and fixed to each other by the structure A, thereby realizing the assembling.

Figure 4:
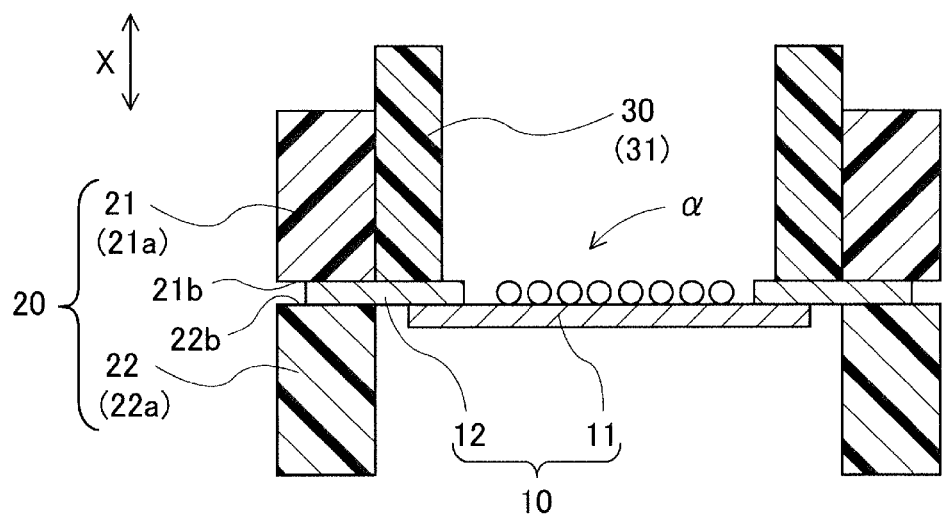
FIG. 4 is a sectional view of the cell culture device of the first embodiment when cells are seeded on one axial end surface of the culture membrane.
Figure 6:
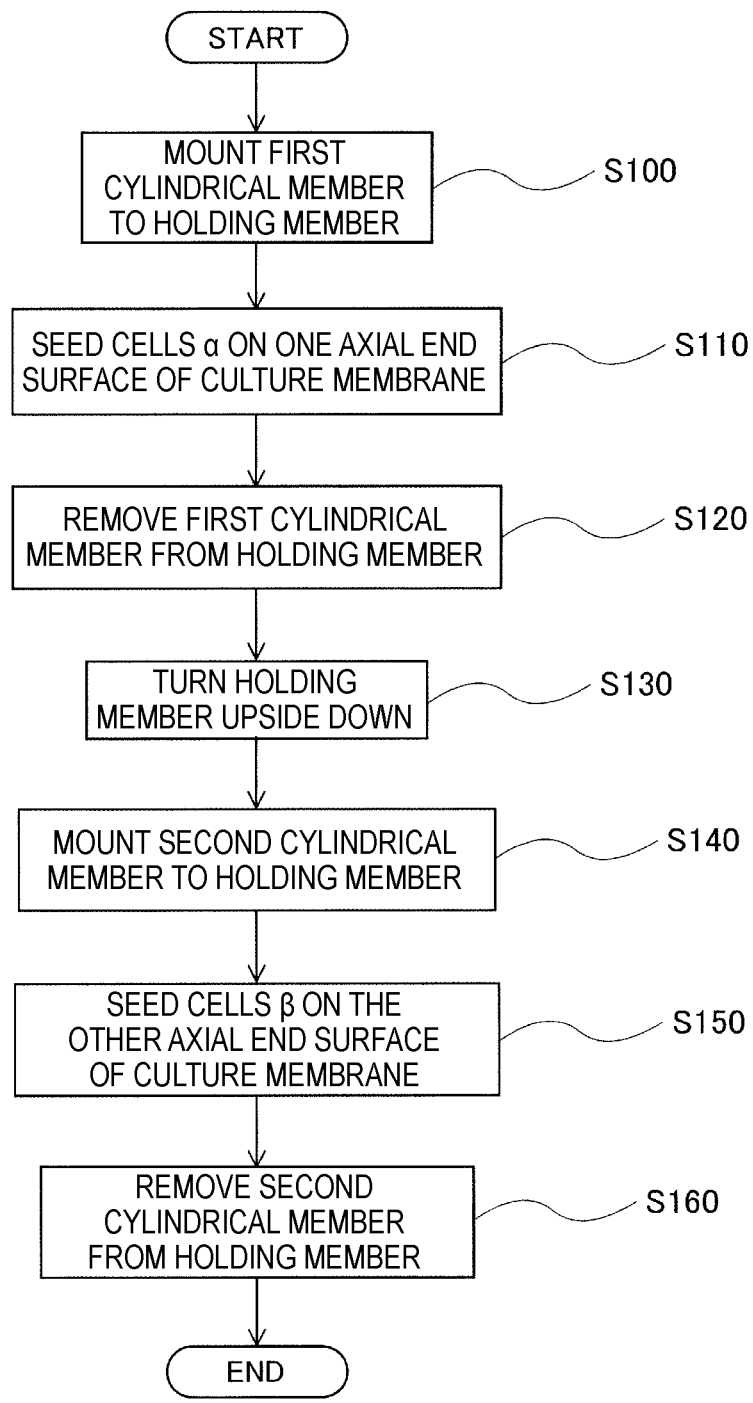
FIG. 6 is a flowchart showing an example of a procedure for using the cell culture device of the first embodiment during double-sided culture.

When such assembling is performed, the first cylindrical member 30 is mounted to the holding member 20, and the first protruding portion 32 protrudes outward from the one axial end of the first holding cylinder 21 of the holding member 20 toward the one axial side (a state shown in FIG. 4 step S100 shown in FIG. 6). The cell culture on the culture membrane 10 is performed on the cell culture device 1 in this state. In the cell culture, the cell culture device 1 may be placed in a well of a plate for the cell culture, filled with a culture solution, and seeded with cells α on the one axial end surface (upper surface shown in FIG. 4) of the culture membrane 10 (specifically, the membrane body 11). The seeding of the cells α is performed by first immersing the cell culture device 1 in the culture solution with the one axial end surface of the culture membrane 10 facing vertically upward, and in this state, supplying the cells α to a space on the one axial end surface side (step S110).

After the seeding of the cells α is completed as described above, the first cylindrical member 30 is removed from the holding member 20 using a jig (step S120), and then the holding member 20 is turned upside down while holding the culture membrane 10 (step S130).

After the holding member 20 is turned upside down, the second cylindrical member 40 is assembled to the holding member 20. First, the second cylindrical member 40 is gripped by a jig in a state in which the holding member 20 is set such that an axial end portion side thereof from which the second cylindrical member 40 is inserted, which is an opposite side to the axial end portion side into which the first cylindrical member 30 is inserted, is positioned upward, then the second cylindrical member 40 is inserted into the holding member 20 by being moved from above in a direction approaching each other in the axial direction X, and thereafter, the holding member 20 and the second cylindrical member 40 are engaged with and fixed to each other by the structure B, thereby realizing the assembling.

Figure 5:
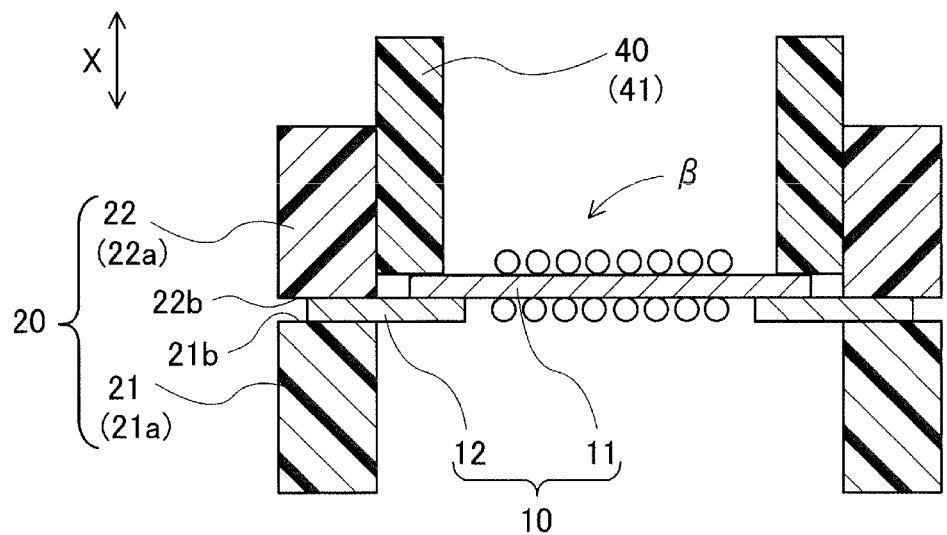
FIG. 5 is a sectional view of the cell culture device of the first embodiment when cells are seeded on the other axial end surface of the culture membrane.

When such assembling is performed, the second cylindrical member 40 is mounted to the holding member 20, and the second protruding portion 42 protrudes outward from the other axial end of the second holding cylinder 22 of the holding member 20 toward the other axial side (a state shown in FIG. 5; step S140). The cell culture on the culture membrane 10 is performed on the cell culture device 1 in this state. In the cell culture, the cell culture device 1 may be placed in a well of a plate for the cell culture, filled with a culture solution, and seeded with cells β on the other axial end surface (upper surface shown in FIG. 5) of the culture membrane 10 (specifically, the membrane body 11). The seeding of the cells α is performed by first immersing the cell culture device 1 in the culture solution with the other axial end surface of the culture membrane 10 facing vertically upward, and in this state, supplying the cells β to a space on the other axial end surface side (step S150).

After the seeding of the cells β is completed as described above, the second cylindrical member 40 is removed from the holding member 20 by using a jig (step S160). Then, the culture membrane 10 on which the cell culture is performed is removed from the holding member 20, and microscopic observation or the like of the membrane body 11 of the culture membrane 10 is performed.

As described above, according to the structure of the cell culture device 1, two types of cells can be seeded on both surfaces of the culture membrane 10 to perform the cell culture. In addition, when two types of cells are seeded on both surfaces of the culture membrane 10, in both cases of seeding cells on the one axial end surface of the culture membrane 10 and seeding cells on the other axial end surface thereof, it is necessary to mount one of the first cylindrical member 30 and the second cylindrical member 40 to an upper side of the holding member 20 holding the culture membrane 10, but it is not necessary to mount the other one of the first cylindrical member 30 and the second cylindrical member 40 to a lower side of the holding member 20. That is, when two types of cells are seeded on both surfaces of the culture membrane 10, the cell culture device 1 can be used in a state of removing either of the first cylindrical member 30 and the second cylindrical member 40 which is positioned on the lower side of the holding member 20 from the holding member 20 without requiring both the first cylindrical member 30 and the second cylindrical member 40 to be mounted to the holding member 20 and them to be used at the same time.

Since the length Lb1 of the first cylindrical member 30 in the axial direction X is larger than the length La1 of the first cylindrical portion 21a of the first holding cylinder 21 in the axial direction X, the first cylindrical member 30 protrudes from the one axial end of the first holding cylinder 21 toward the one axial side at the first protruding portion 32 in the state of being engaged with and fixed to the first holding cylinder 21. Since the length Lb2 of the second cylindrical member 40 in the axial direction X is larger than the length La2 of the second cylindrical portion 22a of the second holding cylinder 22 in the axial direction X, the second cylindrical member 40 protrudes from the other axial end of the second holding cylinder 22 toward the other axial side at the second protruding portion 42 in the state of being engaged and fixed to the second holding cylinder 22. Therefore, according to the cell culture device 1, since a dimensional distance from an axial lower end to the holding portions 21b, 22b holding the culture membrane 10 can be shortened when the cell culture is performed, a volume of the well can be reduced, and cells can be cultured on the culture membrane with a small amount of culture solution.

In the cell culture device 1, the first holding cylinder 21 of the holding member 20 includes the first side surface opening portion 21c penetrating the first cylindrical portion 21a in the radial direction. The second holding cylinder 22 of the holding member 20 includes the second side surface opening portion 22c penetrating the second cylindrical portion 22a in the radial direction. The side surface opening portions 21c, 22c are provided at the predetermined portions including the portions on the lower side in the axial direction X than the culture membrane 10 held by the holding portions 21b, 22b, respectively. Therefore, air accumulated on both surfaces of the culture membrane 10 can be discharged to the outside of the holding member 20 via the side surface opening portions 21c, 22c.

In particular, after cells are seeded on the one axial end surface of the culture membrane 10 held by the holding member 20, when the holding member 20 is turned upside down and cells are seeded on the other axial end surface of the culture membrane 10, air accumulated on the one axial end surface of the culture membrane 10 on which cell seeding has already been performed can be discharged to the outside of the holding member 20 via the side surface opening portion 21c. Therefore, it is possible to prevent air from remaining on a surface on which the cells are initially seeded, and it is possible to avoid inconvenience caused by the air remaining (for example, cells which are initially seeded do not come into contact with the culture solution, or the like).

In the cell culture device 1, the culture membrane 10 includes the membrane body 11 on which cells are seeded, and the support frame 12 joined to the membrane body 11 and formed of a material harder than the membrane body 11. The culture membrane 10 is sandwiched and fixed between the first holding cylinder 21 and the second holding cylinder 22 of the holding member 20 by the support frame 12. Therefore, since the support frame 12 which is relatively hard may be used for handling the culture membrane 10 with a jig, the handling of the culture membrane 10 can be facilitated. In addition, the support frame 12 is formed in an annular shape by being joined to the peripheral edge of the membrane body 11. Therefore, evaluation such as the microscopic observation of the membrane body 11 of the culture membrane 10 can be performed while the support frame 12 is joined to the membrane body 11.

Further, since the first holding cylinder 21 and the second holding cylinder 22 are engaged with and fixed to each other, the holding member 20 sandwiches and holds the culture membrane 10 by the first holding cylinder 21 and the second holding cylinder 22. Therefore, the holding member 20 can be easily assembled while holding the culture membrane 10, and the holding member 20 after assembling can be easily separated into the first holding cylinder 21 and the second holding cylinder 22, so that the culture membrane 10 can be easily taken out from the holding member 20. As a result, the culture membrane 10 after the cell culture can be independently evaluated by the microscopic observation or the like, and the evaluation can be easily and appropriately performed as compared with a structure in which the culture membrane and the holding member are integrated.

In the first embodiment, the first holding portion 21b of the first holding cylinder 21 and the second holding portion 22b of the second holding cylinder 22 each correspond to a "holding portion" described in the claims, respectively.

In the first embodiment, two types of cells are seeded on both surfaces of the culture membrane 10. However, the present invention is not limited to this, and three or more types of cells may be seeded on both surfaces of the culture membrane 10. For example, three types of cells may be prepared, two types of cells may be seeded on one surface of the culture membrane 10, and then the culture membrane 10 may be turned upside down, and the other one type of cells may be seeded on the other surface of the culture membrane 10.

Second Embodiment

Figure 7:
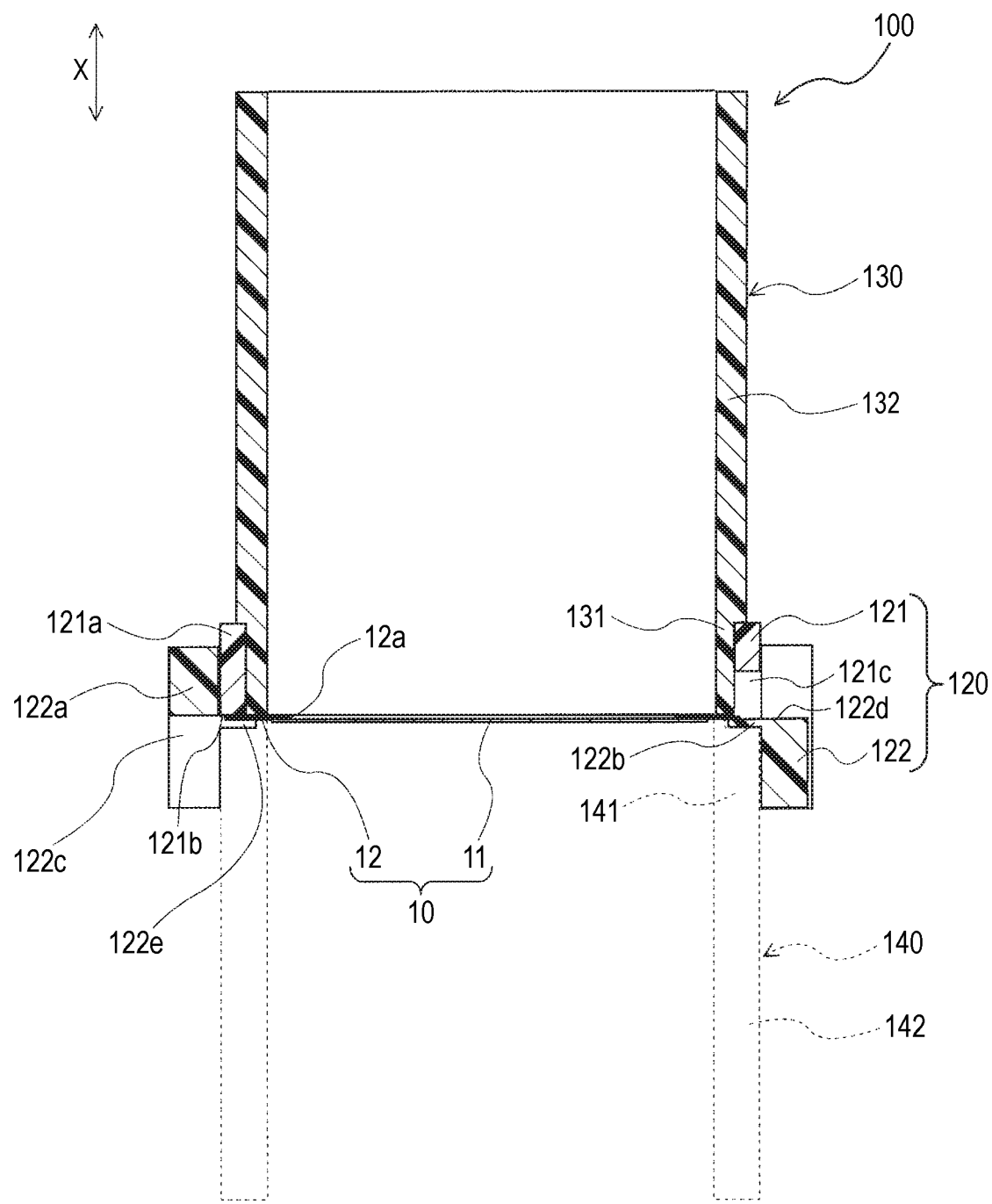
FIG. 7 is a sectional view of a cell culture device according to a second embodiment.

Similarly to the cell culture device 1 of the first embodiment, a cell culture device 100 of a second embodiment can culture two types of cells on both surfaces of the membrane. As shown in FIG. 7, the cell culture device 100 includes the culture membrane 10, a holding member 120, a first cylindrical member 130, and a second cylindrical member 140. Incidentally, in the second embodiment, the same components as those of the cell culture device 1 in the first embodiment are denoted by the same reference numerals, and a description thereof will be omitted or simplified.

Figure 8:
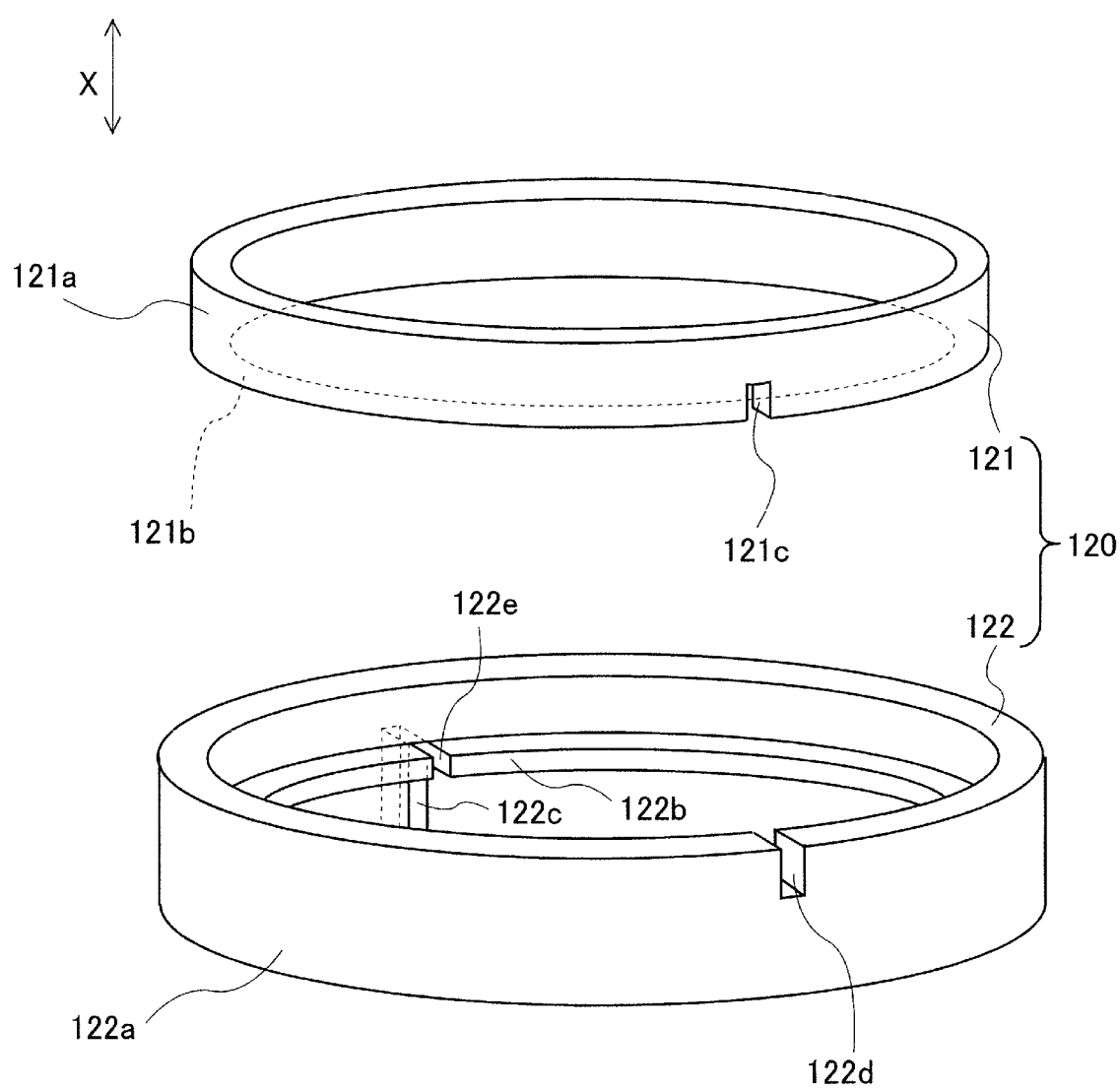
FIG. 8 is an exploded perspective view of a holding member included in the cell culture device of the second embodiment.

The holding member 120 is a member for holding the culture membrane 10. The holding member 120 is formed of a resin material, rubber, or the like. As shown in FIG. 8, the holding member 120 includes two holding cylinders, and has a first holding cylinder 121 and a second holding cylinder 122. The first holding cylinder 121 and the second holding cylinder 122 are arranged adjacent to each other in the axial direction X. The first holding cylinder 121 and the second holding cylinder 122 hold the culture membrane 10 in a state of being engaged with and fixed to each other. The culture membrane 10 held by the holding member 120 is exposed on both axial sides through axial openings of the first holding cylinder 121 and the second holding cylinder 122.

The first holding cylinder 121 and the second holding cylinder 122 are members which are engageably attached to each other, and have a structure in which the first holding cylinder 121 and the second holding cylinder 122 are engaged with and fixed to each other. The engagement structure may be an L-groove engagement structure or a snap-fit type engagement structure similar to the engagement structure 23 of the holding member 20 in the first embodiment. In a state in which the first holding cylinder 121 and the second holding cylinder 122 are engaged with and fixed to each other, a distance in which holding portions of the first holding cylinder 121 and the second holding cylinder 122 facing each other are separated in the axial direction X is set to be smaller than the axial thickness of the culture membrane 10 (specifically, the support frame 12 thereof) before assembling. Accordingly, the support frame 12 of the culture membrane 10 is sandwiched and fixed between the first holding cylinder 121 and the second holding cylinder 122. At this time, gaps between the support frame 12 and the first holding cylinder 121 and between the support frame 12 and the second holding cylinder 122 are sealed.

The first holding cylinder 121 includes a hollow first cylindrical portion 121a extending in a cylindrical shape in the axial direction X, a first holding portion 121b which holds the culture membrane 10, and a first side surface opening portion 121c provided so as to penetrate the first cylindrical portion 121a in the radial direction. The second holding cylinder 122 includes a hollow second cylindrical portion 122a extending in a cylindrical shape in the axial direction X, a second holding portion 122b which holds the culture membrane 10, a second side surface opening portion 122c and a third side surface opening portion 122d provided so as to penetrate the second cylindrical portion 122a in the radial direction, and a holding opening portion 122e provided so as to penetrate the second holding portion 122b in the axial direction X.

The first cylindrical portion 121a has a predetermined length in the axial direction X and has a predetermined thickness in the radial direction. The second cylindrical portion 122a has a predetermined length in the axial direction X and has a predetermined thickness in the radial direction. An outer diameter of the first cylindrical portion 121a and an inner diameter of the second cylindrical portion 122a substantially coincide with each other. The outer diameter of the culture membrane 10 (that is, the outer diameter of the support frame 12) exceeds an inner diameter of the first cylindrical portion 121a and is equal to or less than the outer diameter of the first cylindrical portion 121a, and is equal to or less than the inner diameter of the second cylindrical portion 122a.

The first holding portion 121b is an axial end surface facing the second holding cylinder 122 in the first cylindrical portion 121a. The second holding portion 122b is a flange portion protruding radially inward from the second cylindrical portion 122a. The outer diameter of the culture membrane 10 (that is, the outer diameter of the support frame 12) is larger than an inner diameter of a radially inner end of the second holding portion 122b. The second holding portion 122b is provided at an axial intermediate portion of the second cylindrical portion 122a. The first holding cylinder 121 is engaged with and fixed to the second holding cylinder 122 in a state in which the first cylindrical portion 121a is inserted inside the second cylindrical portion 122a of the second holding cylinder 122 and the first holding portion 121b faces the second holding portion 122b. Accordingly, the first holding cylinder 121 and the second holding cylinder 122 sandwich and hold the culture membrane 10.

The first side surface opening portion 121c is a slit hole portion which is provided so as to penetrate a predetermined portion of the first cylindrical portion 121a in the radial direction, and communicates the inside of the first cylindrical portion 121a to the outside. The first side surface opening portion 121c is provided at one position in the peripheral direction. The predetermined portion in which the first side surface opening portion 121c is provided includes at least a portion on the lower side in the axial direction X than the culture membrane 10 held by the first holding portion 121b during the cell culture in a state in which the first cylindrical portion 121a is positioned below the second cylindrical portion 122a, and is formed to extend from the first holding portion 121b to one axial side. The first side surface opening portion 121c has an air venting function of discharging air accumulated on the lower surface of the culture membrane 10 held by the first holding portion 121b to the outside in a state in which the first cylindrical portion 121a is positioned below the second cylindrical portion 122a.

Each of the second side surface opening portion 122c and the third side surface opening portion 122d is a slit hole portion which is provided so as to penetrate a predetermined portion of the second cylindrical portion 122a in the radial direction, and communicates the inside of the second cylindrical portion 122a to the outside. The second side surface opening portion 122c and the third side surface opening portion 122d are provided at different positions of the second cylindrical portion 122a in the peripheral direction. As a result, a torsional rigidity of the second holding cylinder 122 can be improved and a sealing property can be improved.

The predetermined portion in which the second side surface opening portion 122c is provided includes at least a portion on the lower side in the axial direction X than the culture membrane 10 held by the second holding portion 122b during the cell culture in a state in which the second cylindrical portion 122a is positioned below the first cylindrical portion 121a, and is formed to extend from the second holding portion 122b to the other axial side. The second side surface opening portion 122c has an air venting function of discharging air accumulated on the lower surface of the culture membrane 10 held by the second holding portion 122b to the outside in a state where the second cylindrical portion 122a is positioned below the first cylindrical portion 121a.

The predetermined portion in which the third side surface opening portion 122d is provided includes at least a portion which radially communicates with the first side surface opening portion 121c of the first holding cylinder 121 and is on the lower side in the axial direction X than the culture membrane 10 held by the second holding portion 122b during the cell culture in the state in which the first cylindrical portion 121a is positioned below the second cylindrical portion 122a, and is formed to extend from the second holding portion 122b to the one axial side. The third side surface opening portion 122d has an air venting function which communicates with the first side surface opening portion 121c and discharges air accumulated on the lower surface of the culture membrane 10 held by the second holding portion 122b to the outside in the state in which the first cylindrical portion 121a is positioned below the second cylindrical portion 122a.

The holding opening portion 122e is provided so as to penetrate the second holding portion 122b in the axial direction X, and communicates with the second side surface opening portion 122c in the radial direction. The holding opening portion 122e has an air venting function which communicates with the second side surface opening portion 122c and discharges air accumulated on the lower surface of the culture membrane 10 held by the second holding portion 122b to the outside in the state in which the second cylindrical portion 122a is positioned below the first cylindrical portion 121a.

Each of the first cylindrical member 130 and the second cylindrical member 140 is a cylindrical member attached to the holding member 120. The first cylindrical member 130 and the second cylindrical member 140 are each formed of a resin material, rubber, or the like. The first cylindrical member 130 and the second cylindrical member 140 are selectively attached to the holding member 20 when cells are cultured on the culture membrane 10. That is, the first cylindrical member 130 is attached to the holding member 120 when the first cells are seeded on one axial end surface of the culture membrane 10, while the second cylindrical member 140 is attached to the holding member 120 when the second cells are seeded on the other axial end surface of the culture membrane 10.

The first cylindrical member 130 includes a hollow cylindrical portion 131 extending in a cylindrical shape in the axial direction X. The first cylindrical member 130 is mounted on one axial side of the holding member 120 (specifically, the first holding cylinder 121). The first cylindrical member 130 can be attached to/detached from the first holding cylinder 121. The first cylindrical member 130 and the first holding cylinder 121 have a structure in which the first cylindrical member 130 and the first holding cylinder 121 are engaged with and fixed to each other. The culture membrane 10 held by the holding member 120 is exposed to one axial side through an axial opening of the first cylindrical member 130.

The first cylindrical member 130 is formed so as to be insertable into the first holding cylinder 121 of the holding member 120. The first cylindrical member 130 is attached in a state of being inserted into the first cylindrical portion 121a of the first holding cylinder 121. The first cylindrical member 130 is formed such that an inner diameter thereof is invariable over the entire area in the axial direction X, but an outer diameter thereof on the other axial side is smaller than an outer diameter thereof on one axial side. The outer diameter on the other axial side coincides with the inner diameter of the first holding cylinder 121. The cylindrical portion 131 of the first cylindrical member 130 includes a first protruding portion 132 which protrudes from one axial end of the first holding cylinder 121 toward the one axial side in a state of being engaged with and fixed to the other axial side of the first holding cylinder 121.

The first cylindrical member 130 is formed such that an axial end surface of the cylindrical portion 131 on the insertion side abuts against the one axial end surface of the culture membrane 10 sandwiched and fixed between the first holding cylinder 121 and the second holding cylinder 122, and an axial end surface of the cylindrical portion 131 on an opposite side to the insertion side is arranged at a position protruding toward the one axial side from the one axial end of the first holding cylinder 121, in the state in which the first cylindrical member 130 is engaged with and fixed to the first holding cylinder 121. That is, a length of the first cylindrical member 130 in the axial direction X is set to be larger than a length of the first cylindrical portion 121a of the first holding cylinder 121 in the axial direction X.

The second cylindrical member 140 includes a hollow cylindrical portion 141 extending in a cylindrical shape in the axial direction X. The second cylindrical member 140 is mounted on the other axial side of the holding member 120 (specifically, the second holding cylinder 122). The second cylindrical member 140 can be attached to/detached from the second holding cylinder 122. The second cylindrical member 140 and the second holding cylinder 122 have a structure in which the second cylindrical member 140 and the second holding cylinder 122 are engaged with and fixed to each other. The culture membrane 10 held by the holding member 120 is exposed to the other axial side through an axial opening of the second cylindrical member 140.

The second cylindrical member 140 is formed to be insertable into the second holding cylinder 122 of the holding member 120. The second cylindrical member 140 is attached in a state of being inserted into the second cylindrical portion 122a of the second holding cylinder 122. The second cylindrical member 140 has an outer diameter which coincides with the inner diameter of the second cylindrical portion 122a of the second holding cylinder 122. The second cylindrical portion 141 of the second cylindrical member 140 includes a second protruding portion 142 Which protrudes from the other axial end of the second holding cylinder 122 to the other axial side in a state of being engaged with and fixed to the second holding cylinder 122.

The second cylindrical member 140 is formed such that an axial end surface of the cylindrical portion 141 on the insertion side abuts against the other axial end surface of the culture membrane 10 sandwiched and fixed between the first holding cylinder 121 and the second holding cylinder 122 and abuts against the second holding portion 122b having a flange shape, and an axial end surface of the cylindrical portion 141 on an opposite side to the insertion side is arranged at a position protruding toward the other axial side from the other axial end of the second holding cylinder 122, in the state in which the second cylindrical member 140 is engaged with and fixed to the second holding cylinder 122. That is, a length of the second cylindrical member 140 in the axial direction X is set to be larger than a length of the second cylindrical portion 122a of the second holding cylinder 122 in the axial direction X.

As an assembling procedure of the cell culture device 100 having the above structure, first, the first cylindrical member 130 is assembled to the holding member 120 holding the culture membrane 10, as in the case of the cell culture device 1 of the first embodiment. Then, the cells are seeded on the one axial end surface of the culture membrane 10 in a state in which the first protruding portion 132 protrudes outward from the one axial end of the first holding cylinder 121 of the holding member 120 toward the one axial side. After the cell seeding is completed, the first cylindrical member 130 is removed from the holding member 120, and then the holding member 120 is turned upside down while holding the culture membrane 10.

Next, the second cylindrical member 140 is assembled to the holding member 120. Then, the cells are seeded on the other axial end surface of the culture membrane 10 in a state in which the second protruding portion 142 protrudes outward from the other axial end of the second holding cylinder 122 of the holding member 120 toward the other axial side. After the cell seeding is completed, the second cylindrical member 140 is removed from the holding member 120, and then the microscopic observation or the like of the membrane body 11 of the culture membrane 10 is performed.

As described above, even in the structure of the cell culture device 100, two types of cells can be seeded on both surfaces of the culture membrane 10 to perform the cell culture. In addition, when two types of cells are seeded on both surfaces of the culture membrane 10, the cell culture device 100 can be used in a state of removing either of the first cylindrical member 130 and the second cylindrical member 140 which is positioned on the lower side of the holding member 120 without requiring both the first cylindrical member 130 and the second cylindrical member 140 to be mounted and used at the same time. The first cylindrical member 130 and the second cylindrical member 140 protrude outward in the axial direction X from the axial ends of the holding member 120 by the protruding portions 132, 142 in a state of being engaged with and fixed to the holding member 120, respectively. Therefore, according to the cell culture device 100, since a dimensional distance from an axial lower end to the holding portions 121b, 122b holding the culture membrane 10 can be shortened when the cell culture is performed, the volume of the well can be reduced, and cells can be cultured on the culture membrane with a small amount of culture solution.

In the cell culture device 100, the first holding cylinder 121 of the holding member 120 includes the first side surface opening portion 121c penetrating the first cylindrical portion 121a in the radial direction. The second holding cylinder 122 of the holding member 120 includes the second side surface opening portion 122c and the third side surface opening portion 122d penetrating the second cylindrical portion 122a in the radial direction and the holding opening portion 122e penetrating the second holding portion 122b in the axial direction X. The side surface opening portions 121c, 122c and 122d are provided at the respective predetermined portions including portions on the lower side in the axial direction X than the culture membrane 10 held by the holding portions 121b, 122b when cells are cultured on both surfaces of the culture membrane 10, respectively. In particular, the third side surface opening portion 122d is provided so as to expose the lower surface of the culture membrane 10 held by the holding portions 121b, 122b to the outside of the second holding cylinder 122 via the first side surface opening portion 121c when cells are seeded on the other axial end surface of the culture membrane 10. In addition, the holding opening portion 122e is provided so as to expose the lower surface of the culture membrane 10 held by the holding portions 121b, 122b to the outside of the second holding cylinder 122 via the second side surface opening portion 122c when cells are seeded on the one axial end surface of the culture membrane 10. Therefore, air accumulated on both surfaces of the culture membrane 10 can be discharged to the outside of the holding member 120 via the side surface opening portions 121c, 122c.

In the second embodiment, the first holding portion 121b of the first holding cylinder 121 and the second holding portion 122b of the second holding cylinder 122 each correspond to the "holding portion" described in the claims, respectively.

Figure 9:
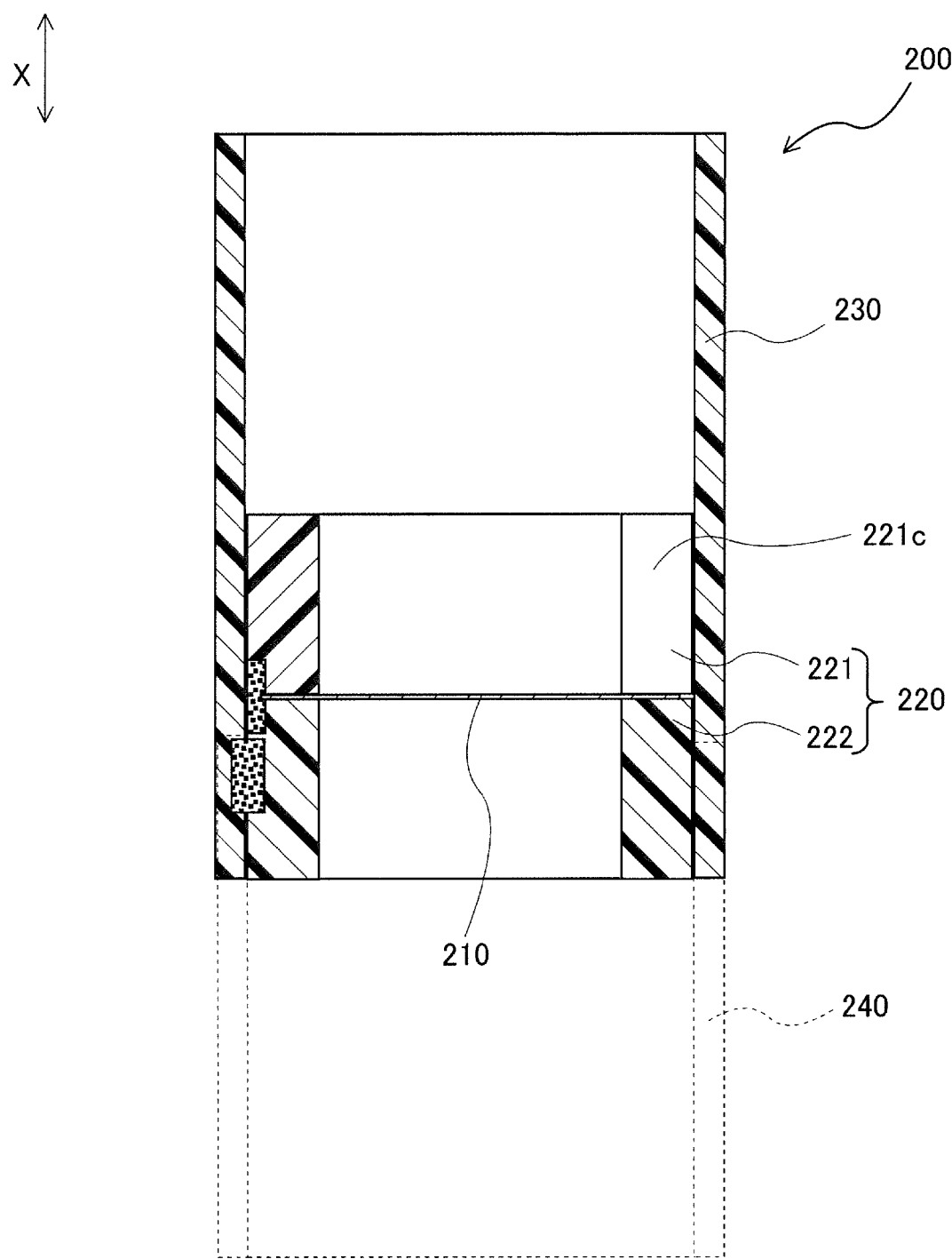
FIG. 9 is a sectional view of a cell culture device according to a modification.
Figure 10:
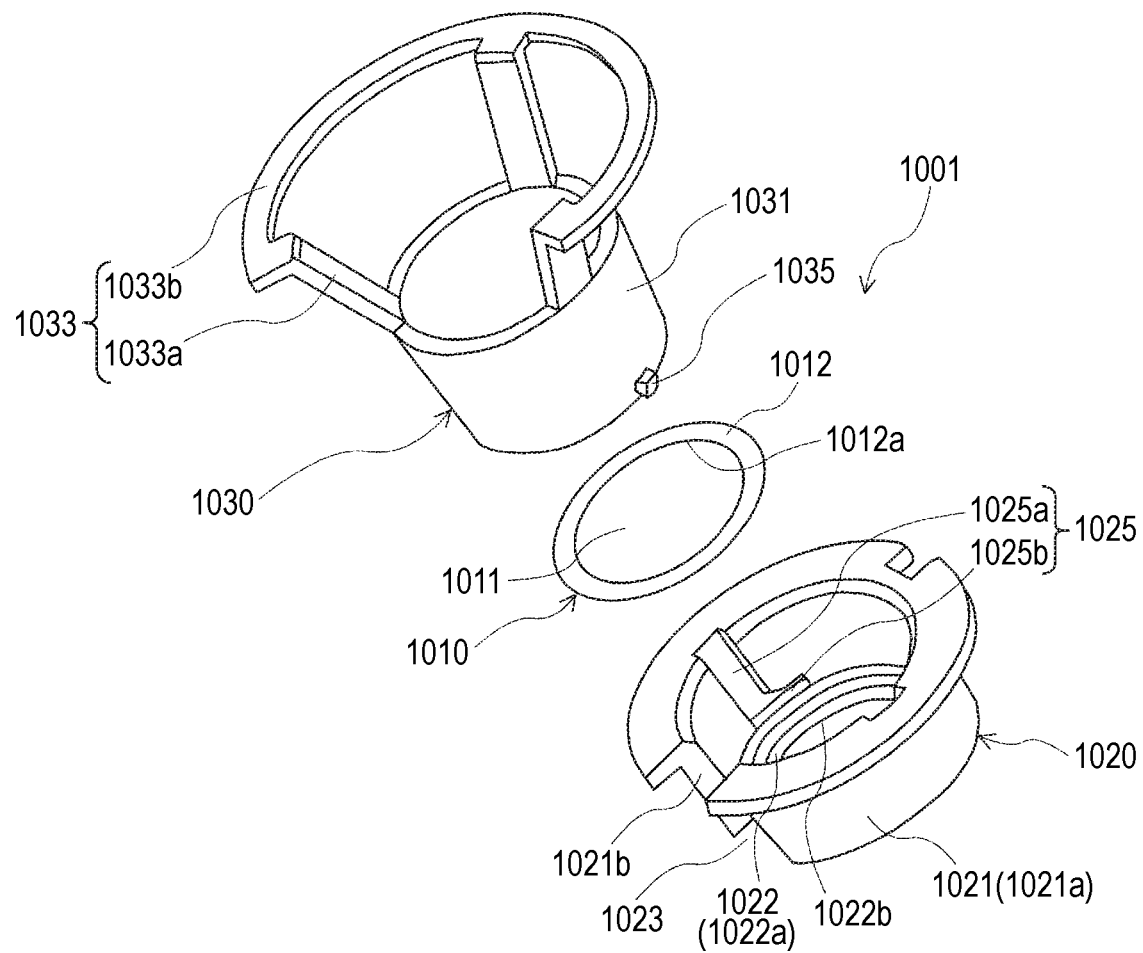
FIG. 10 is an exploded perspective view of a cell culture device according to a third embodiment.
Figure 11:
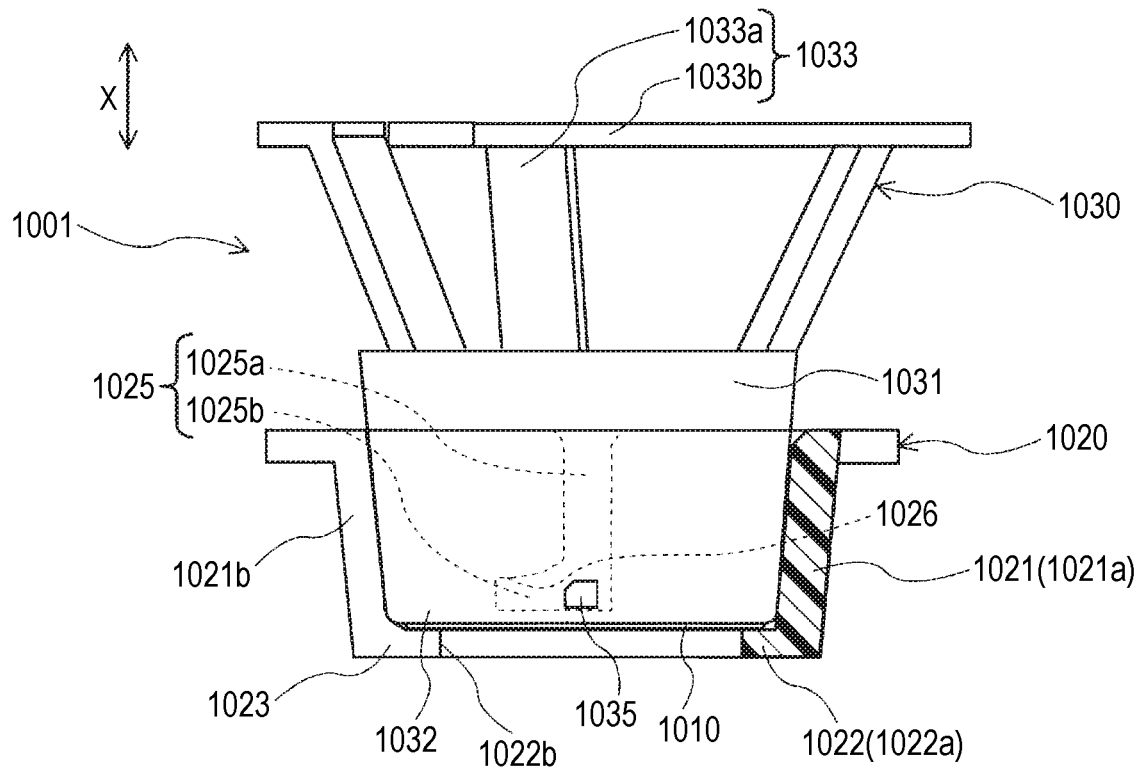
FIG. 11 is a side view (a partially sectional view) of the cell culture device of the third embodiment.
Figure 12:
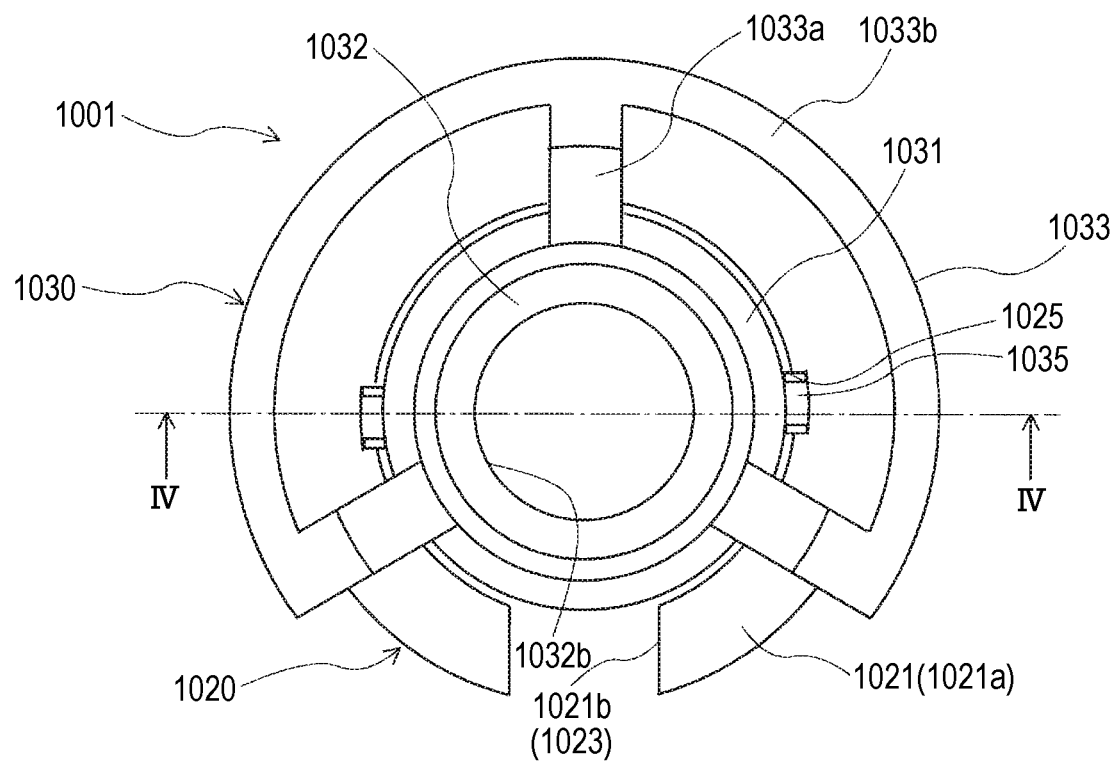
FIG. 12 is a top view of the cell culture device of the third embodiment.
Figure 13:
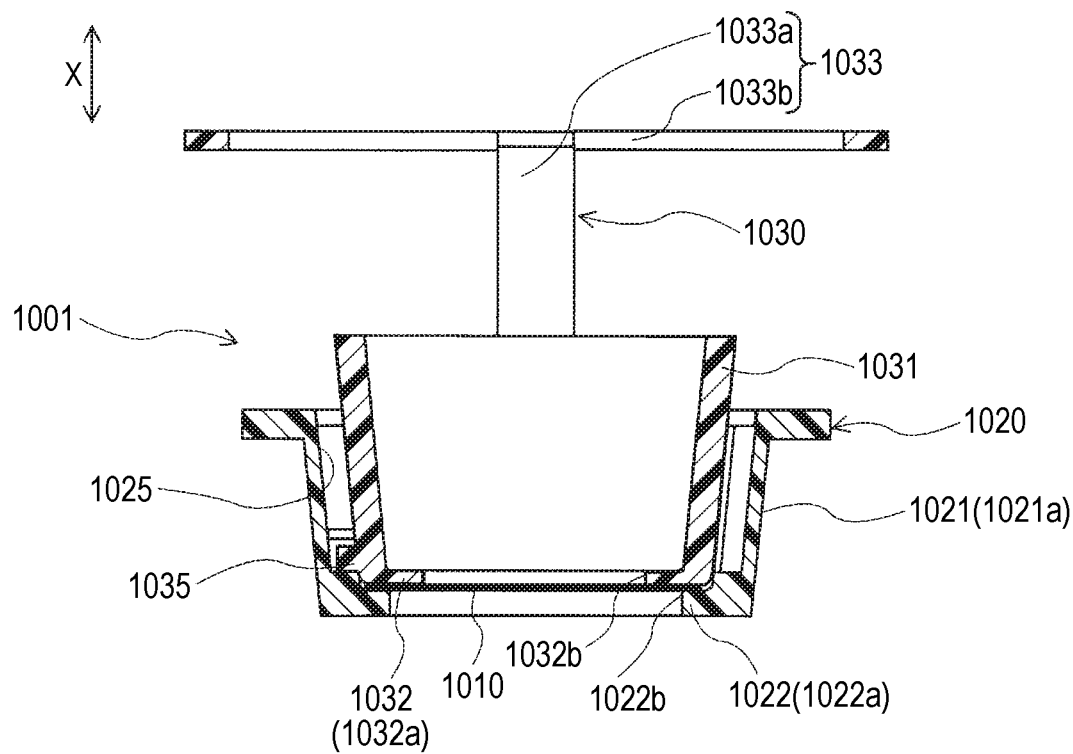
FIG. 13 is a sectional view of the cell culture device of the third embodiment taken along a line IV-IV shown in FIG. 12.

In the first and second embodiments described above, the cell culture devices 1, 100 are used in which the cylindrical members 30, 40, 130, and 140 are inserted and arranged inside cylinders of the holding members 20, 120. However, the present invention is not limited to this, and as shown in FIG. 9, the present invention may be applied to a cell culture device 200 in which cylindrical members 230, 240 are inserted and arranged outside a cylinder of a holding member 220.

In the first and second embodiments described above, both of the two holding cylinders 21, 22 constituting the holding member 20 and both of the holding cylinders 121, 122 constituting the holding member 120 are respectively provided with the opening portions 21c, 22c, 121c, 122c, 122d, and 122e which discharge air accumulated on the lower surface of the culture membrane 10 to the outside. However, the present invention is not limited to this, and only in order to discharge air accumulated on the one axial end surface of the culture membrane 10 to the outside of the holding members 20, 120 when cells are seeded on the other axial end surface of the culture membrane 10 after the holding members 20, 120 are turned upside down, a holding cylinder 221 of two holding cylinders 221, 222 positioned below when cells are seeded on the other axial end surface of the culture membrane 10 may be provided with an opening portion 221c for discharging air accumulated on the lower surface of the culture membrane 10 to the outside as shown in FIG. 9.

In the first and second embodiments described above, the culture membrane 10 includes the membrane body 11 and the annular support frame 12 joined to the peripheral edge of the membrane body 11. However, the present invention is not limited to this, and the support frame 12 may be formed in, for example, a cross shape or a net shape when viewed from the axial direction X as long as the support frame 12 has a frame-like structure joined to the membrane body 11.

In the first and second embodiments described above, the culture membrane 10 includes the membrane body 11 and the support frame 12 joined to the peripheral edge of the membrane body 11. However, the present invention is not limited to this, and as shown in FIG. 9, the culture membrane 210 may be formed only of a membrane body having no support frame. In this modification, the culture membrane 210 may be joined and fixed to either of the first holding cylinder 221 and the second holding cylinder 222 of the holding member 220. In this modification, an outer diameter of the culture membrane 210 may be larger than inner diameters of the first holding cylinder 221 and the second holding cylinder 222 and equal to or less than outer diameters of the first holding cylinder 221 and the second holding cylinder 222. In addition, in this modification, it is preferable that peripheral surfaces between the holding cylinders 221, 222 and cylindrical members 230, 240 are sealed in order to ensure an inside/outside sealing property of an periphery of the first holding cylinder 221 holding the culture membrane 210 and an inside/outside sealing property of an periphery of the second holding cylinder 222 holding the culture membrane 210 when cells are cultured.

Further, in the first and second embodiments described above, the cylindrical members 30, 40, 130, and 140 are formed such that the axial end surfaces thereof on the insertion side abut against the support frame 12 of the culture membrane 10 when the cylindrical members 30, 40, 130, and 140 are mounted to the holding members 20, 120, respectively. However, the present invention is not limited to this, and the axial end surfaces of the cylindrical members 30, 40, 130, and 140 may not abut against the support frame 12 of the culture membrane 10 when the cylindrical members 30, 40, 130, and 140 are mounted to the holding members 20, 120, respectively.

Third Embodiment

A cell culture device 1001 of a third embodiment is a device for culturing anchorage-dependent cells. The cell culture device 1001 is capable of culturing two types of cells on both surfaces of a membrane. As shown in FIGS. 10, 11, 12, and 13, the cell culture device 1001 includes a culture membrane 1010, a first member 1020, and a second member 1030. In the cell culture device 1001, the culture membrane 1010 is sandwiched and fixed between the first member 1020 and the second member 1030.

The culture membrane 1010 is a sheet-like membrane on which cells are cultured. The culture membrane 1010 includes a membrane body 1011 and a support frame 1012. The membrane body 1011 is a membrane main body portion serving as a scaffold for cells when cells are cultured. The membrane body 1011 is a porous membrane provided with pores on both surfaces thereof. The membrane body 1011 is formed of a thermosetting resin such as polyurethane, silicone resin, phenol resin, epoxy resin, unsaturated polyester, or polyimide. A thickness of the membrane body 1011 is, for example, 0.1 µm to 110 µm.

The support frame 1012 is a base material which supports and reinforces the membrane body 1011. The support frame 1012 is an annular frame body having a circular hole 1012a opened in a center portion thereof. The support frame 1012 is joined and fixed to a peripheral edge of the membrane body 1011. Incidentally, a shape of the support frame 1012 may include at least an annular frame body portion, and may further include a protruding portion protruding radially outward from a part of the frame portion in a peripheral direction. The protruding portion has a function for facilitating handling when a person grips the culture membrane 1010 with a jig such as a tweezer, for example. The support frame 1012 is formed of a material harder than the membrane body 1011. The material of the support frame 1012 is, for example, a thermoplastic resin such as polyethylene, polypropylene, ABS resin, acrylic resin, and polyethylene terephthalate (PET), or a thermosetting elastomer such as silicone rubber. A thickness of the support frame 1012 is, for example, 0.05 mm to 0.5 mm.

The first member 1020 is a base material for sandwiching and fixing the culture membrane 1010. The first member 1020 is a member formed in a cylindrical shape. The first member 1020 is formed of a resin material, rubber, or the like. The first member 1020 includes a first cylindrical portion 1021, a placing portion 1022, and a side surface opening portion 1023. The first cylindrical portion 1021 and the placing portion 1022 are formed integrally with each other.

The first cylindrical portion 1021 is a hollow portion extending in a cylindrical shape in the axial direction X. The first cylindrical portion 1021 is formed in a cylindrical shape, for example. Incidentally, an inner diameter of the first cylindrical portion 1021 may be constant regardless of a position thereof in the axial direction X, or may vary (more specifically, be larger as the position in the axial direction X is farther from the placing portion 1022) depending on the position thereof in the axial direction X. The first cylindrical portion 1021 includes a peripheral wall portion 1021a. An inner peripheral surface of the peripheral wall portion 1021a is formed to be able to guide the culture membrane 1010 in the axial direction X to the placing portion 1022.

The peripheral wall portion 1021a includes a cutout portion 1021b. The cutout portion 1021b penetrates the peripheral wall portion 1021a in the radial direction and extends in the axial direction X. The cutout portion 1021b extends in the axial direction X from an axial end portion of the first cylindrical portion 1021 where the culture membrane 1010 is inserted into the first member 1020 in the axial direction X to a portion where the placing portion 1022 is provided. The cutout portion 1021b is provided in a portion of the peripheral wall portion 1021a in the peripheral direction, and is provided at one position on the peripheral wall portion 1021a. The cutout portion 1021b is a slit for inserting a jig for attaching and detaching the culture membrane 1010 sandwiched between the first member 1020 and the second member 1030 to and from the placing portion 1022 from the radial outside. That is, the cutout portion 1021b has a function of allowing the jig inserted from the radial outside to the first member 1020 to be movable in the axial direction X.

The placing portion 1022 is a portion on which the culture membrane 1010 is placed. The placing portion 1022 is connected to one axial end of the first cylindrical portion 1021. The placing portion 1022 is formed in an annular shape on an inner peripheral side of one axial end of the first cylindrical portion 1021. Incidentally, the placing portion 1022 may be provided intermittently in the peripheral direction on the inner peripheral side of the one axial end of the first cylindrical portion 1021. The placing portion 1022 includes a wall portion 1022a on which an axial end surface facing in the axial direction X is formed, and a circular hole portion 1022b which is opened at a central portion of the wall portion 1022a. The placing portion 1022 abuts against the support frame 1012 of the culture membrane 1010 at an inner axial end surface of the wall portion 1022a to hold the culture membrane 1010. The culture membrane 1010 held on the wall portion 1022a of the placing portion 1022 is exposed to the outside through the hole portion 1022b of the placing portion 1022.

The side surface opening portion 1023 is provided so as to penetrate the peripheral wall portion 1021a of the first cylindrical portion 1021 in the radial direction. The side surface opening portion 1023 is a hole portion which allows the inside of the first cylindrical portion 1021 to communicate with the outside. The side surface opening portion 1023 is provided at a portion of the peripheral wall portion 1021a in the peripheral direction, and is provided at a predetermined portion of the peripheral wall portion 1021a. The predetermined portion at which the side surface opening portion 1023 is provided includes at least a portion closer to the placing portion 1022 side in the axial direction X than the culture membrane 1010 placed on the placing portion 1022. The side surface opening portion 1023 has an air venting function of discharging air accumulated on the lower surface of the culture membrane 1010 placed on the placing portion 1022 to the outside. The side surface opening portion 1023 is provided at the same peripheral position as the cutout portion 1021b in the first member 1020. The side surface opening portion 1023 is arranged so as to be continuous with the cutout portion 1021b in the axial direction X, and is integrated with the cutout portion 1021b.

The second member 1030 is paired with the first member 1020 and a base material for sandwiching and fixing the culture membrane 1010. The second member 1030 is a member formed in a cylindrical shape. The second member 1030 is inserted and arranged in the first cylindrical portion 1021 of the first member 1020. The second member 1030 is formed of a resin material, rubber, or the like. The second member 1030 includes a second cylindrical portion 1031, a facing portion 1032, and a gripping portion 1033. The second cylindrical portion 1031, the facing portion 1032, and the gripping portion 1033 are formed integrally with each other.

The second cylindrical portion 1031 is a hollow portion extending in a cylindrical shape in the axial direction X. The second cylindrical portion 1031 is formed in a cylindrical shape, for example. An outer diameter of the second cylindrical portion 1031 has a size which substantially coincides with the inner diameter of the first cylindrical portion 1021 of the first member 1020. Incidentally, an inner diameter or the outer diameter of the second cylindrical portion 1031 may be constant regardless of a position thereof in the axial direction X, or may vary depending on the position thereof in the axial direction X (more specifically, be larger as the position in the axial direction X is farther from the placing portion 1022).

The facing portion 1032 is a portion facing the wall portion 1022a of the placing portion 1022 of the first member 1020 in the axial direction X. The facing portion 1032 has a function of sandwiching the culture membrane 1010 with the placing portion 1022 of the first member 1020. The facing portion 1032 is connected to one axial end of the second cylindrical portion 1031. The facing portion 1032 is formed in an annular shape on an inner peripheral side of the one axial end of the second cylindrical portion 1031. Incidentally, the facing portion 1032 may be provided intermittently in the peripheral direction on the inner peripheral side of the one axial end of the second cylindrical portion 1031.

The facing portion 1032 includes a wall portion 1032a on which an axial end surface facing in the axial direction X is formed, and a circular hole portion 1032b which is opened at a central portion of the wall portion 1032a. The facing portion 1032 abuts against the support frame 1012 of the culture membrane 1010 at an outer axial end surface of the wall portion 1032a to hold the culture membrane 1010. The culture membrane 1010 sandwiched between the placing portion 1022 and the facing portion 1032 is exposed to an inner space of the second cylindrical portion 1031 through the hole portion 1032b of the facing portion 1032.

The gripping portion 1033 has a function of facilitating handling of the second member 1030 when a person assembles the second member 1030 to the first member 1020 with a jig such as a tweezer. The gripping portion 1033 includes an arm portion 1033a and a connection portion 1033b. A plurality of (for example, three) arm portions 1033a are provided. One end of each of the arm portions 1033a is connected to the other axial end of the second cylindrical portion 1031 on an opposite side to the facing portion 1032 in the axial direction. The arm portions 1033a are arranged at intervals in the peripheral direction of the second cylindrical portion 1031. The arm portion 1033a extends outward in the axial direction X from the other axial end of the second cylindrical portion 1031. The connection portion 1033b is formed in an annular shape so as to connect the other ends of the plurality of arm portions 1033a. The connection portion 1033b is cut out at a part in the peripheral direction, and is formed in a C shape.

Figure 14:
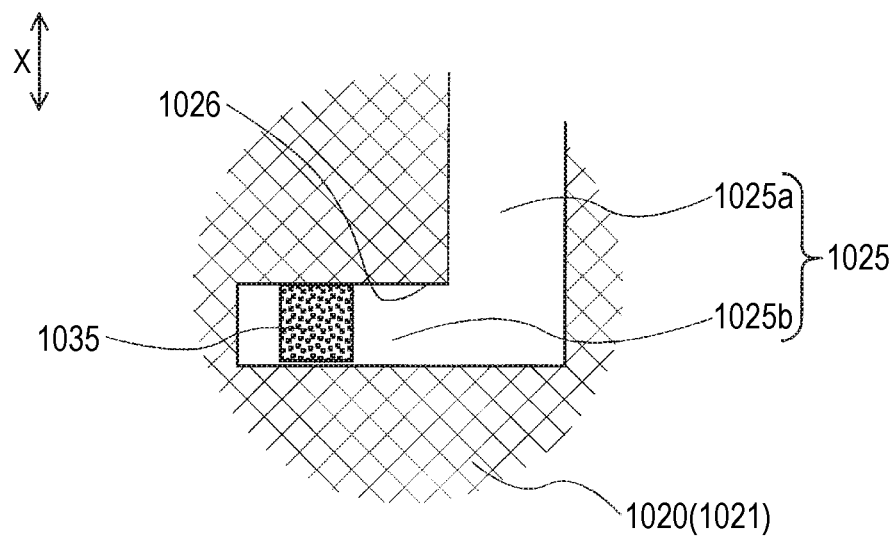
FIG. 14 is a view for explaining locking portions of a first member and a second member included in the cell culture device of the third embodiment.

The first member 1020 and the second member 1030 each have a locking portion which restricts a relative movement between the first member 1020 and the second member 1030 in the axial direction X by which the first member 1020 and the second member 1030 are separated from each other in an assembled state. That is, the first member 1020 includes a concave portion 1025 as a locking portion, and the second member 1030 includes a convex portion 1035 as the locking portion. As shown in FIG. 14, the concave portion 1025 and the convex portion 1035 restrict the relative movement between the first member 1020 and the second member 1030 in the axial direction X by which the first member 1020 and the second member 1030 are separated from each other in the assembled state of the first member 1020 to the second member 1030.

The concave portion 1025 of the first member 1020 is a groove portion provided on an inner surface of the peripheral wall portion 1021a of the first cylindrical portion 1021 so as to be recessed radially outward. The concave portions 1025 are provided at two peripheral positions (for example, different positions by 180°) of the first member 1020, for example. The concave portion 1025 is formed in an L shape. That is, the concave portion 1025 includes an axial parallel portion 1025a extending in the axial direction X and an orthogonal portion 1025b extending in a direction orthogonal to the axial direction X. The axial parallel portion 1025a and the orthogonal portion 1025b each have a width greater than or equal to a width of the convex portion 1035 of the second member 1030. The axial parallel portion 1025a extends from the other axial end on an opposite side to the placing portion 1022 of the first cylindrical portion 1021 to the one axial end side. The orthogonal portion 1025b is connected to one axial end portion of the axial parallel portion 1025a and extends in the orthogonal direction. The orthogonal portion 1025b forms a locking wall 1026 on the other axial end side to which the convex portion 1035 of the second member 1030 is locked.

The convex portion 1035 of the second member 1030 is a protruding portion provided on an outer surface of the second cylindrical portion 1031 so as to protrude radially outward. The convex portions 1035 are provided at two peripheral positions (for example, different positions by) 180° of the second member 1030, for example. The convex portion 1035 is formed to have a size corresponding to the concave portion 1025 (particularly, the orthogonal portion 1025b). Specifically, the convex portion 1035 has a width (that is, an axial length) corresponding to the width (that is, an axial length) of the orthogonal portion 1025b of the concave portion 1025.

Figure 15:
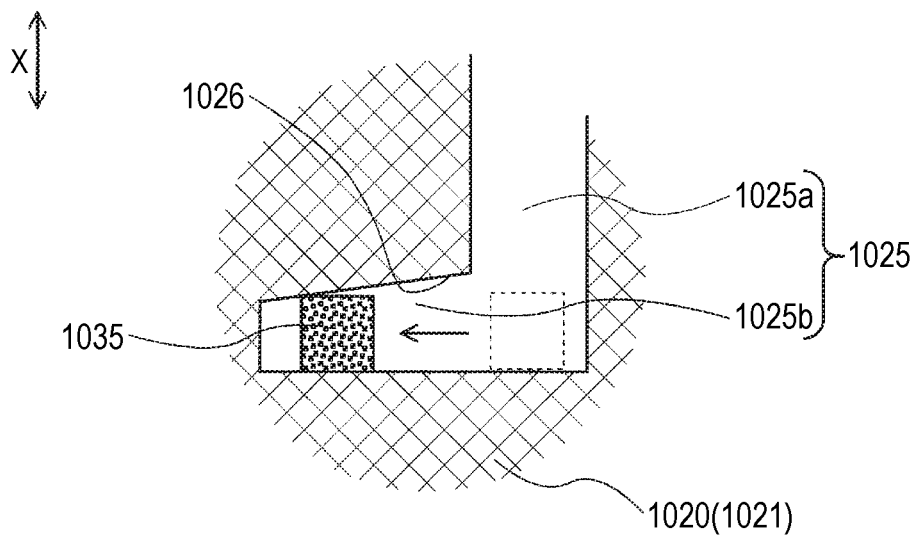
FIG. 15 is a view for explaining locking portions of a first member and a second member included in a cell culture device according to a modification.

Incidentally, the width of the orthogonal portion 1025b of the concave portion 1025 may vary depending on a peripheral position thereof. For example, as shown in FIG. 15, the width of the orthogonal portion 1025b may be the widest on a side close to the axial parallel portion 1025a such that the convex portion 1035 is easily moved from the side close to the axial parallel portion 1025a to an inner side far from the axial parallel portion 1025a in the orthogonal portion 1025b when the first member 1020 and the second member 1030 are assembled, and may be gradually narrowed toward the inner side far from the axial parallel portion 1025a. In addition, the width of the orthogonal portion 1025b is set to a width of a predetermined position on the inner side of the orthogonal portion 1025b at which the convex portion 1035 is fitted being wider than the minimum width position, so that the predetermined position is closer to the axial parallel portion 1025a than the minimum width position. Therefore, the convex portion 1035 is difficultly moved from the predetermined position to the side close to the axial parallel portion 1025a after the convex portion 1035 is fitted at the predetermined position.

The assembling of the first member 1020 and the second member 1030 is performed such that the convex portion 1035 moves along the concave portion 1025. The convex portion 1035 can be fitted into the vicinity of a tip end side of the concave portion 1025 and locked to the locking wall 1026. The first member 1020 and the second member 1030 are assembled to each other by fitting the convex portion 1035 into the concave portion 1025 and being locked to the locking wall 1026, thereby restricting the relative movement between the first member 1020 and the second member 1030 in the axial direction X by which the first member 1020 and the second member 1030 are separated from each other.

In a state in which the assembling of the first member 1020 and the second member 1030 is completed by fitting the convex portion 1035 into the concave portion 1025, a distance between the placing portion 1022 and the facing portion 1032 in the axial direction X is set to be smaller than the thickness of the support frame 1012 of the culture membrane 1010 before the assembling. Therefore, in a state in which the assembling is completed, the culture membrane 1010 is sandwiched between the placing portion 1022 of the first member 1020 and the facing portion 1032 of the second member 1030.

Next, assembling of the cell culture device 1001 will be described.

The culture membrane 1010, the first member 1020, and the second member 1030, which are components of the cell culture device 1001, are prepared. The cell culture device 1001 is assembled manually by a person using a jig such as a tweezer. In an assembling procedure, first, the culture membrane 1010 is assembled to the first member 1020. The culture membrane 1010 is gripped with a jig, the culture membrane 1010 is then inserted into the first member 1020 by being moved in the axial direction X from the opposite side to the placing portion 1022 of the first member 1020 in the axial direction, and thereafter, the culture membrane 1010 is placed so as to abut against the axial end surface of the placing portion 1022 of the first member 1020, thereby realizing the assembling of the culture membrane 1010 to the first member 1020. Incidentally, the assembling of the culture membrane 1010 to the first member 1020 described above may be performed in a state in which the first member 1020 is set with the axial end portion thereof on a placing portion 1022 side being positioned below.

Next, as described above, the second member 1030 is assembled to the first member 1020 on which the culture membrane 1010 is placed on the placing portion 1022. First, the gripping portion 1033 of the second member 1030 is gripped by a jig, the second member 1030 is then inserted into the first member 1020 by being moved in a direction approaching each other in the axial direction X from the opposite side to the placing portion 1022 of the first member 1020 in the axial direction, the convex portion 1035 of the second member 1030 is moved along the axial parallel portion 1025*a* of the recess 1025 of the first member 1020, and thereafter, the second member 1030 is moved in one peripheral direction with respect to the first member 1020, and the convex portion 1035 of the second member 1030 is moved along the orthogonal portion 1025*b* of the concave portion 1025 of the first member 1020, thereby realizing the assembling. Incidentally, the assembling of the second member 1030 to the first member 1020 described above may be performed by inserting the second member 1030 from above the first member 1020 in a state in which the first member 1020 is set with the axial end portion thereof on the placing portion 1022 side being positioned below.

When the movement is performed and the convex portion 1035 of the second member 1030 is fitted into the vicinity of the tip end side of the concave portion 1025 of the first member 1020, the relative movement of the two members 1020, 1030 in the axial direction X by which the two members 1020, 1030 are separated from each other is restricted, and the two members 1020, 1030 are mounted to each other, so that the assembling of the two members 1020, 1030 is completed. When the assembling of the two members 1020, 1030 is completed, the placing portion 1022 and the facing portion 1032 sandwich the culture membrane 1010 (specifically, the support frame 1012) therebetween, and the convex portion 1035 of the second member 1030 is locked to the locking wall 1026 of the concave portion 1025 of the first member 1020.

According to the structure of the cell culture device 1001, after the first member 1020 and the second member 1030 are assembled, the relative movement between the first member 1020 and the second member 1030 in the axial direction X can be restricted by the concave portion 1025 and the convex portion 1035 as the locking portions in a state in which the support frame 1012 of the culture membrane 1010 is sandwiched between the first member 1020 and the second member 1030. Therefore, adhesiveness in the assembled state of the first member 1020 and the second member 1030 sandwiching the culture membrane 1010 can be improved, and a sealing property on both sides sandwiching the culture membrane 1010 during cell culture can be ensured. Although the culture membrane 1010 positioned in the side surface opening portion 1023 is not sandwiched between the first member 1020 and the second member 1030, since an area is narrow, the culture membrane 1010 is sealed only by an elastic pressing force of the support frame 1012 and the second member 1030.

After the assembling of the first member 1020 and the second member 1030 is completed as described above, the cell culture is performed on one surface of the culture membrane 1010. In the cell culture, the cell culture device 1001 may be placed in a well of a plate for cell culture and be filled with a culture solution. The cell culture on the one surface of the culture membrane 1010 is performed by first immersing the cell culture device 1001 in the culture solution with one surface of the culture membrane 1010 on the second member 1030 side facing vertically upward, and in this state, supplying first cells to a space on one surface side.

When the culture of the first cells is completed as described above, the assembling of the first member 1020 and the second member 1030 of the cell culture device 1001 is released, and the first member 1020 and the second member 1030 are assembled again by turning the culture membrane 1010 upside down. The releasing of the assembling of the first member 1020 and the second member 1030 is performed in a reverse procedure to the assembling procedure described above. Specifically, the releasing of the assembling is realized by first moving the second member 1030 in the other peripheral direction with respect to the first member 1020, and then moving the second member 1030 in a direction away from the first member 1020 in the axial direction X. When the assembling is released, next, the culture membrane 1010 is moved in the axial direction X by the jig from the state in which the culture membrane 1010 is placed on the placing portion 1022 of the first member 1020, is then turned upside down, and is placed again so as to abut against the axial end surface of the placing portion 1022. Further, as described above, the second member 1030 is assembled to the first member 1020 on which the culture membrane 1010 is placed on the placing portion 1022.

When the assembling is completed, the placing portion 1022 and the facing portion 1032 sandwich the culture membrane 1010 therebetween, and the convex portion 1035 of the second member 1030 is locked to the locking wall 1026 of the concave portion 1025 of the first member 1020, so that the same effect as described above can be obtained. After the assembling is completed, the cell culture is performed on the other surface of the culture membrane 1010. The cell culture on the other surface of the culture membrane 1010 is performed by first immersing the cell culture device 1001 in the culture solution with the other surface of the culture membrane 1010 on the second member 1030 side facing vertically upward, and in this state, supplying second cells to a space on the other surface side.

As described above, according to the structure of the cell culture device 1001, two types of cells can be cultured on both surfaces of the culture membrane 1010. In addition, when two types of cells are cultured on both surfaces of the culture membrane 1010, after the cells are cultured on one side of the culture membrane 1010, the culture membrane 1010 itself may be turned upside down after the assembling of the first member 1020 and the second member 1030 is released, and it is not necessary to turn the first member 1020 and the second member 1030 upside down. Therefore, it is possible to improve a workability in culturing two types of cells on both surfaces of the culture membrane 1010.

In addition, when two types of cells are cultured on both surfaces of the culture membrane 1010, it is not necessary to make the cell culture device vertically symmetrical in consideration of the upside down of the culture membrane 1010. Therefore, a structure of the first member 1020 on the placing portion 1022 side in the axial direction X with respect to the culture membrane 1010 placed on the placing portion 1022 can be simplified, the cell culture device 1001 can be reduced in a size, and a size of the well and the amount of the culture solution can be reduced in realizing the cell culture. Further, since the culture membrane 1010 can be removed from the first member 1020 and the second member 1030 independently, the culture membrane 1010 after the cell culture can be independently evaluated by the microscopic observation or the like, and the evaluation can be easily and appropriately performed as compared with a structure in which the culture membrane and a holding member are integrated.

In the cell culture device 1, the first member 1020 includes the cutout portion 1021b which penetrates the peripheral wall portion 1021a of the first cylindrical portion 1021 in the radial direction and extends in the axial direction X. The cutout portion 1021b is a slit for inserting a jig such as a tweezer from the radial outside of the first member 1020 and moving the jig in the axial direction X. The culture membrane 1010 is placed on the placing portion 1022 of the first member 1020 and is sandwiched between the first member 1020 and the second member 1030, and can be gripped by a jig such as a tweezer inserted from the cutout portion 1021b for attaching and detaching the culture membrane 1010 to and from the placing portion 1022. Therefore, the culture membrane 1010 can be easily attached to and detached from the placing portion 1022 of the first member 1020 using a jig, and the cell culture can be performed on both surfaces of the culture membrane 1010 with a minimum configuration without requiring many components as the cell culture device 1001 to be prepared for realizing the cell culture on both sides of the culture membrane 1010.

The first member 1020 includes the side surface opening portion 1023 which penetrates the peripheral wall portion 1021a of the first cylindrical portion 1021 in the radial direction. The side surface opening portion 1023 is provided at the predetermined portion of the peripheral wall portion 1021a including at least a portion closer to the placing portion 1022 side in the axial direction X than the culture membrane 1010 placed on the placing portion 1022. Therefore, after the first cells are cultured on the one surface of the culture membrane 1010, when the culture membrane 1010 is turned upside down and the second cells are cultured on the other surface thereof, air accumulated on a surface on which the first cells are cultured can be discharged to the outside of the first member 1020 via the side surface opening portion 1023, so that it is possible to prevent air from remaining on the surface on which the first cells are initially seeded, and it is possible to avoid inconvenience caused by the air remaining (for example, the first cells do not come into contact with the culture solution, or the like).

The cutout portion 1021b and the side surface opening portion 1023 described above are provided at the same position in the peripheral direction on the first member 1020, and are arranged so as to be continuous with each other in the axial direction X and integrated with each other. Therefore, a mold structure of the first member 1020 provided with the cutout portion 1021b and the side surface opening portion 1023 can be simplified, and the first member 1020 can be manufactured accurately and easily.

In the third embodiment, the concave portion 1025 of the first member 1020 and the convex portion 1035 of the second member 1030 each correspond to a "locking portion" described in the claims.

In the third embodiment, the cutout portion 1021b and the side surface opening portion 1023 of the first member 1020 are provided at the same position in the peripheral direction, and are arranged so as to be continuous with each other in the axial direction X. However, the present invention is not limited to this, and the cutout portion 1021b and the side surface opening portion 1023 of the first member 1020 may be provided at positions different from each other in the peripheral direction, and may be arranged so as not to be continuous with each other in the axial direction X. According to a structure of this modification, a torsional rigidity of the first member 1020 in the peripheral direction can be ensured as compared with the structure of the third embodiment.

In the third embodiment, the first member 1020 includes the concave portion 1025 provided on the inner surface of the peripheral wall portion 1021a of the first cylindrical portion 1021 so as to be recessed radially outward, and the second member 1030 includes the convex portion 1035 provided on the outer surface of the second cylindrical portion 1031 so as to protrude radially outward. However, the present invention is not limited to this, and the first member 1020 may include a convex portion provided on the inner surface of the first cylindrical portion 1021 so as to protrude radially inward, and the second member 1030 may include a concave portion provided on the outer surface of the second cylindrical portion 1031 so as to be recessed radially outward.

In the third embodiment, two types of cells are seeded on both surfaces of the culture membrane 1010. However, the present invention is not limited to this, and three or more types of cells may be seeded on both surfaces of the culture membrane 1010. For example, three types of cells may be prepared, two types of cells may be seeded on one surface of the culture membrane 1010, and then the culture membrane 1010 may be turned upside down, and the other one type of cells may be seeded on the other surface of the culture membrane 1010.

Fourth Embodiment

Similarly to the cell culture device 1001 of the third embodiment, a cell culture device 1100 of a fourth embodiment is a device for culturing anchorage-dependent cells. Hereinafter, in the cell culture device 1100, the same components as those of the cell culture device 1001 are denoted by the same reference numerals, and a description thereof will be omitted or simplified.

Figure 16:
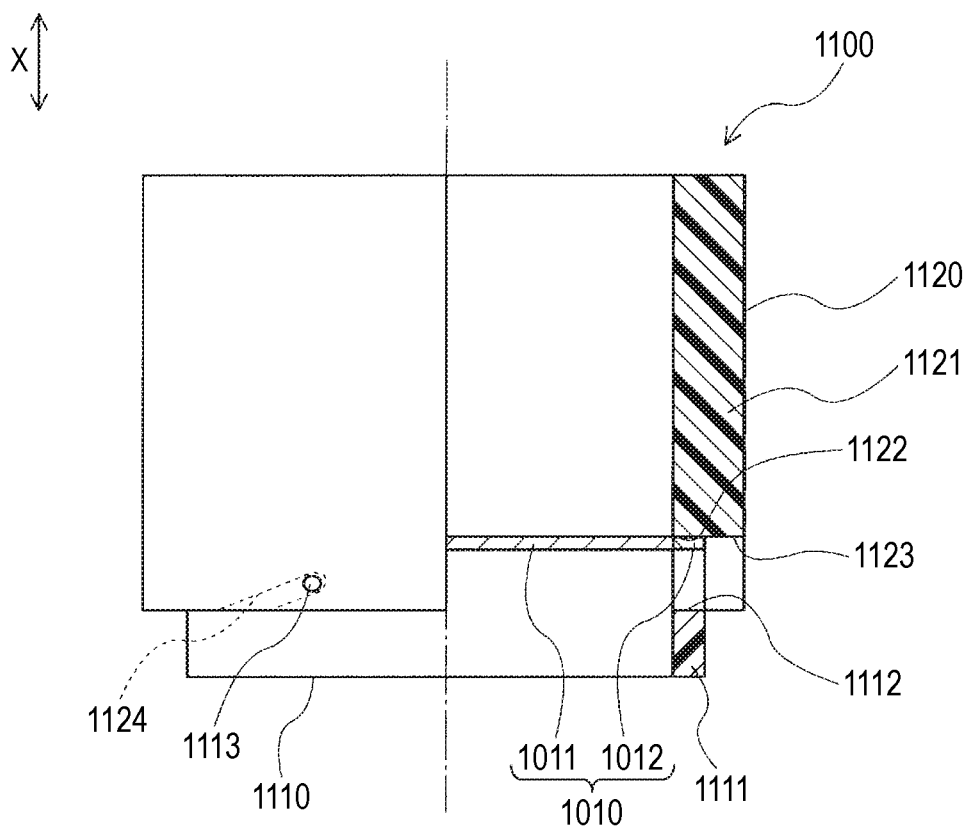
FIG. 16 is a side view (left half) and a sectional view (right half) of the cell culture device according to a fourth embodiment.

As shown in FIG. 16, the cell culture device 1100 includes the culture membrane 1010, the first member 1110, and the second member 1120. In the cell culture device 1100, the culture membrane 1010 is sandwiched and fixed between the first member 1110 and the second member 1120.

Each of the first member 1110 and the second member 1120 is a base material for sandwiching and fixing the culture membrane 1010. Each of the first member 1110 and the second member 1120 is a member formed in a cylindrical shape. Each of the first member 1110 and the second member 1120 is formed of a resin material, rubber, or the like.

The first member 1110 includes a first cylindrical portion 1111 extending in a cylindrical shape in the axial direction X, a placing portion (not shown), and a side surface opening portion 1112 penetrating the first cylindrical portion 1111 in the radial direction. The side surface opening portion 1112 is provided at a predetermined portion of the first cylindrical portion 1111 including at least a portion closer to the placing portion side (a lower side in FIG. 16) in the axial direction X than the culture membrane 1010 placed on the placing portion. Incidentally, the placing portion may be an axial end surface of the first cylindrical portion 1111 facing the axial direction X.

The second member 1120 is arranged so as to be externally inserted into a part of the first cylindrical portion 1111 of the first member 1110. The second member 1120 includes a second cylindrical portion 1121 extending in a cylindrical shape in the axial direction X, a facing portion 1122 facing the placing portion of the first member 1110 in the axial direction X, and a side surface opening portion 1123 penetrating the first cylindrical portion 1111 in the radial direction. The facing portion 1122 is formed in an annular shape on an inner peripheral side of one axial end (the lower end in FIG. 16) of the second cylindrical portion 1121. The facing portion 1122 abuts against the support frame 1012 of the culture membrane 1010 at an axial end surface to hold the culture membrane 1010. Incidentally, the facing portion 1122 may be an axial end surface of the second cylindrical portion 1121 facing the axial direction X.

The side surface opening portion 1123 is provided at a portion of the second cylindrical portion 1121 in the peripheral direction, and is provided at a predetermined portion of the second cylindrical portion 1121. The side surface opening portion 1123 communicates with the side surface opening portion 1112 of the first member 1110. The predetermined portion at which the side surface opening portion 1123 is provided includes at least a portion closer to the placing portion side (the lower side in FIG. 16) in the axial direction X than the culture membrane 1010 placed on the placing portion. The side surface opening portion 1123 has, together with the side surface opening portion 1112 of the first member 1110, an air venting function of discharging air accumulated on the lower surface of the culture membrane 1010 placed on the placing portion to the outside.

The first member 1110 and the second member 1120 each have a locking portion which restricts a relative movement between the first member 1110 and the second member 1120 in the axial direction X by which the first member 1110 and the second member 1120 are separated from each other in an assembled state thereof. That is, the first member 1110 includes a convex portion 1113 as the locking portion, and the second member 1120 includes a concave portion 1124 serving as the locking portion. The convex portion 1113 and the concave portion 1124 restrict the relative movement between the first member 1110 and the second member 1120 in the axial direction X by which the first member 1110 and the second member 1120 are separated from each other in an assembled state of the first member 1110 to the second member 1120.

The convex portion 1113 is a protruding portion provided on an outer surface of the first cylindrical portion 1111 so as to protrude radially outward. The convex portions 1113 are provided at two peripheral positions (for example, different positions by 180°) of the first member 1110, for example. The convex portion 1113 is formed to have a size corresponding to the concave portion 1124. Specifically, the convex portion 1113 has a width corresponding to a width of the concave portion 1124.

The concave portion 1124 is a groove portion provided on an inner surface of the second cylindrical portion 1121 so as to be recessed radially outward. The concave portion 1124 is formed at one axial end portion of the second cylindrical portion 1121. The concave portions 1124 are provided at two peripheral positions (for example, different positions by 180°) of the second member 1120, for example. The concave portion 1124 is formed to be inclined with respect to the axial direction X. That is, the concave portion 1124 is formed in a spiral shape so as to extend in the axial direction X while extending in the peripheral direction. The innermost portion of the concave portion 1124 forms a locking wall to which the convex portion 1113 of the first member 1110 is locked.

The assembling of the first member 1110 and the second member 1120 is performed such that the convex portion 1113 moves along the concave portion 1124. The convex portion 1113 can be fitted into the innermost portion of the concave portion 1124 and locked to the locking wall. The first member 1110 and the second member 1120 are assembled to each other by fitting the convex portion 1113 into the concave portion 1124 and being locked to the locking wall, thereby restricting the relative movement between the first member 1110 and the second member 1120 in the axial direction X by which the first member 1110 and the second member 1120 separated from each other.

Next, assembling of the cell culture device 1100 will be described.

The culture membrane 1010, the first member 1110, and the second member 1120, which are components of the cell culture device 1100, are prepared. The cell culture device 1100 is assembled manually by a person using a jig such as a tweezer. In an assembling procedure, first, the culture membrane 1010 is assembled to the first member 1110. The culture membrane 1010 is gripped with a jig, the culture membrane 1010 is then moved in the axial direction X with respect to the first member 1110 and placed so as to abut against the axial end surface of the placing portion of the first member 1110, thereby realizing the assembling of the culture membrane 1010 to the first member 1110. Incidentally, the assembling of the culture membrane 1010 to the first member 1110 described above may be performed in a state in which the first member 1110 is set with the axial end portion thereof on the placing portion side being positioned above.

Next, as described above, the second member 1120 is assembled to the first member 1110 on which the culture membrane 1010 is placed on the placing portion. First, with a jig, the second member 1120 is externally inserted into the first member 1110 by being moving in a direction approaching each other in the axial direction X and is rotated in the peripheral direction, and the convex portion 1113 of the first member 1110 is moved along the concave portion 1124 of the second member 1120, thereby realizing the assembling. Incidentally, the assembling of the second member 1120 to the first member 1110 described above may be performed by inserting the second member 1120 from above the first member 0 in a state in which the first member 1110 is set with the axial end portion thereof on the placing portion side being positioned above.

When the movement is performed and the convex portion 1113 of the first member 1110 is fitted into the innermost portion of the concave portion 1124 of the second member 1120, the relative movement of the two members 1110, 1120 in the axial direction X by which the two members 1110, 1120 are separated from each other is restricted, and the two members 1110, 1120 are mounted to each other, so that the assembling of the two members 1110, 1120 is completed. When the assembling of the two members 1110, 1120 is completed, the placing portion and the facing portion 1122 sandwich the culture membrane 1010 (specifically, the support frame 1012) therebetween, and the convex portion 1113 of the first member 1110 is locked to the locking wall of the concave portion 1124 of the second member 1120.

According to the structure of the cell culture device 1100, after the first member 1110 and the second member 1120 are assembled, the relative movement between the first member 1110 and the second member 1120 in the axial direction X can be restricted by the convex portion 1113 and the concave portion 1124 as the locking portions in a state in which the support frame 1012 of the culture membrane 1010 is sandwiched between the first member 1110 and the second member 1120. Therefore, adhesiveness in the assembled state of the first member 1110 and the second member 1120 sandwiching the culture membrane 1010 can be improved, and a sealing property on both sides sandwiching the culture membrane 1010 during the cell culture can be ensured.

After the assembling of the first member 1110 and the second member 1120 is completed as described above, the cell culture is performed on both surfaces of the culture membrane 1010 in the same manner as in the third embodiment. Therefore, according to the cell culture device 1100, the same effects as those of the cell culture device 1001 of the third embodiment can be obtained.

In the fourth embodiment, the convex portion 1113 of the first member 1110 and the concave portion 1124 of the second member 1120 each correspond to the "locking portion" described in the claims.

In the fourth embodiment, the first member 1110 includes the convex portion 1113 provided on the outer surface of the first cylindrical portion 1111 so as to protrude radially outward, and the second member 1120 includes the concave portion 1124 provided on the inner surface of the second cylindrical portion 1121 so as to be recessed radially outward. However, the present invention is not limited to this, and the first member 1110 may have a concave portion provided on the outer surface of the first cylindrical portion 1111 so as to be recessed radially inward, and the second member 1120 may have a convex portion provided on inner surface of the second cylindrical portion 1121 so as to protrude radially inward.

Fifth Embodiment

Similarly to the cell culture device 1001 of the third embodiment, a cell culture device 1200 of a fifth embodiment is a device for culturing anchorage-dependent cells. Hereinafter, in the cell culture device 1200, the same components as those of the cell culture device 1001 are denoted by the same reference numerals, and a description thereof will be omitted or simplified.

Figure 17:
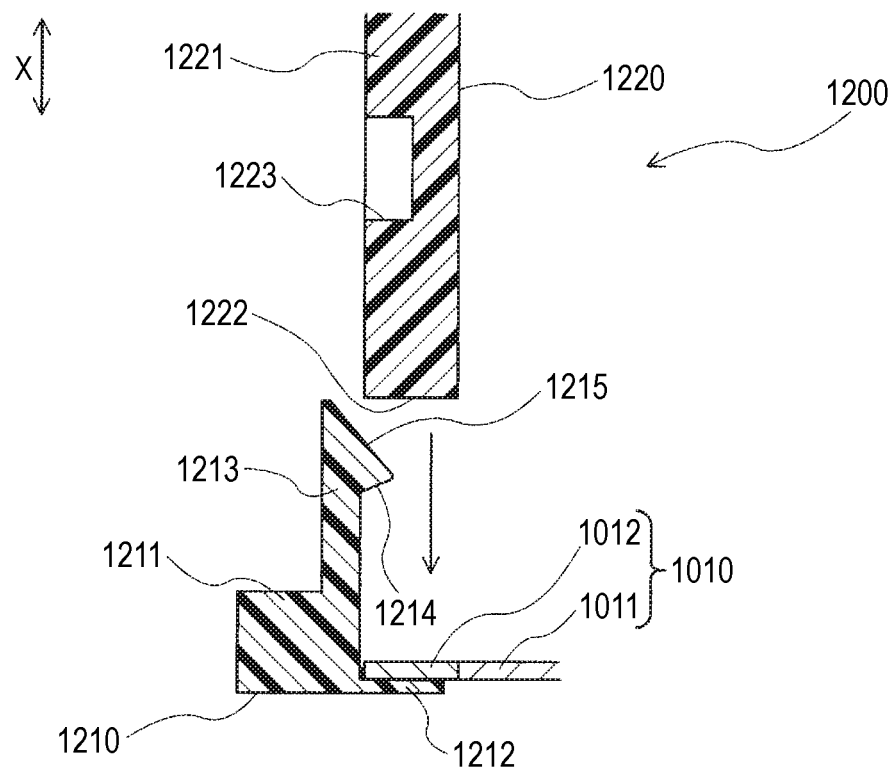
FIG. 17 is a view showing a state before locking of locking portions of a first member and a second member included in a cell culture device according to a fifth embodiment.
Figure 18:
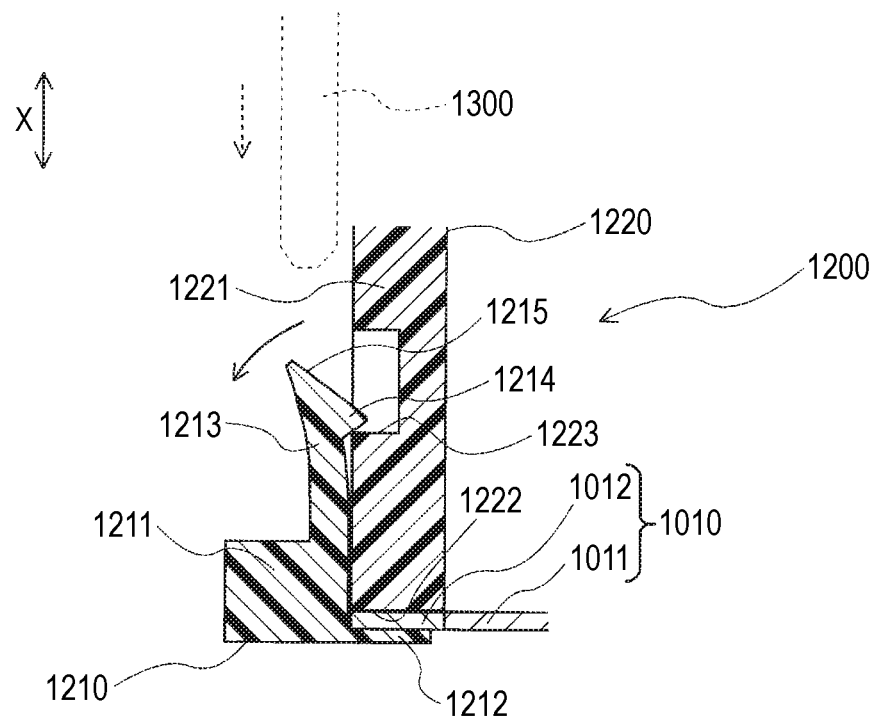
FIG. 18 is a view showing a state after the locking of the locking portions of the first member and the second member included in the cell culture device according to the fifth embodiment.

As shown in FIGS. 17 and 18. the cell culture device 1200 includes the culture membrane 10, a first member 1210, and a second member 1220. In the cell culture device 1200, the culture membrane 1010 is sandwiched and fixed between the first member 1210 and the second member 1220.

Each of the first member 1210 and the second member 1220 is a base material for sandwiching and fixing the culture membrane 1010. Each of the first member 1210 and the second member 1220 is a member formed in a cylindrical shape. Each of the first member 1210 and the second member 1220 is formed of a resin material, rubber, or the like.

The first member 1210 includes a first cylindrical portion 1211 extending in a cylindrical shape in the axial direction X and a placing portion 1212 on which the culture membrane 1010 is placed, similar to the first cylindrical portion 1021 and the placing portion 1022 of the first member 1020 of the third embodiment. The second member 1220 is inserted and arranged in the first cylindrical portion 1211 of the first member 1210, similar to the second cylindrical portion 1031 and the facing portion 1032 of the second member 1030 of the third embodiment. The second member 1220 includes a second cylindrical portion 1221 extending in a cylindrical shape in the axial direction X, and a facing portion 1222 facing the placing portion 1212 of the first member 1210 in the axial direction X.

The first member 1210 and the second member 1220 each have a locking portion which restricts a relative movement in the axial direction X by which the first member 1210 and the second member 1220 are separated from each other in an assembled state thereof. The locking portion is a so-called snap-fit type locking portion. That is, the first member 1210 includes an elastic deformation portion 1213 as the locking portion, and the second member 1220 includes a groove portion 1223 as the locking portion. The elastic deformation portion 1213 and the groove portion 1223 restrict the relative movement in the axial direction X by which the first member 1210 and the second member 1220 are separated from each other in the assembled state of the first member 1210 to the second member 1220.

The elastic deformation portion 1213 is a portion extending in a plate shape from an axial end surface of the first cylindrical portion 1211 in the axial direction X. The elastic deformation portion 1213 can be elastically deformed in the radial direction. The elastic deformation portion 1213 is provided at two peripheral positions (for example, different positions by 180°) of the first member 1210, for example. A claw portion 1214 is provided at an axial tip end portion of the elastic deformation portion 1213. The claw portion 1214 is a hooking portion protruding radially inward from a plate-shaped main body of the elastic deformation portion 1213. A radially inner surface of the claw portion 1214 forms an inclined surface 1215 inclined in a tapered shape. A radial width of the claw portion 1214 is set to be the maximum at a root side and gradually decrease toward an axial tip end.

The groove portion 1223 is provided on an outer surface of the second cylindrical portion 1221 so as to be recessed radially inward. The groove portion 1223 is formed in the middle of the second cylindrical portion 1221 in the axial direction. The groove portion 1223 is a portion where the claw portion 1214 is hooked when the first member 1210 and the second member 1220 approach each other in the axial direction X to a predetermined positional relationship. The groove portions 1223 are provided at two peripheral positions (for example, different positions by 180°) of the second member 1220, for example. The groove portion 1223 is formed to have a size corresponding to the claw portion 1214 of the elastic deformation portion 1213 of the first member 1210. The groove portion 1223 forms a locking wall to which the claw portion 1214 of the first member 1210 is hooked and locked.

As shown in FIGS. 17 and 18, the assembling of the first member 1210 and the second member 1220 is performed by relatively moving the first member 1210 and the second member 1220 in the axial direction X such that the claw portion 1214 of the elastic deformation portion 1213 is hooked by the groove portion 1223. The first member 1210 and the second member 1220 are assembled to each other by the claw portion 1214 being hooked and locked to the groove portion 1223, thereby restricting the relative movement between the first member 1210 and the second member 1220 in the axial direction X by which the first member 1210 and the second member 1220 are separated from each other.

Next, assembling of the cell culture device 1200 will be described.

The culture membrane 1010, the first member 1210, and the second member 1220, which are components of the cell culture device 1200, are prepared. The cell culture device 1200 is assembled manually by a person using a jig such as a tweezer. In an assembling procedure, first, the culture membrane 1010 is assembled to the first member 1210. The culture membrane 1010 is gripped with a jig, the culture membrane 1010 is then moved in the axial direction X with respect to the first member 1210 and placed so as to abut against the axial end surface of the placing portion 1212 of the first member 1210, thereby realizing the assembling of the culture membrane 1010 to the first member 1210. Incidentally, the assembling of the culture membrane 1010 to the first member 1210 described above may be performed in a state in which the first member 1210 is set with the axial end portion thereof on the placing portion side being positioned above.

Next, as described above, the second member 1220 is assembled to the first member 1210 on which the culture membrane 1010 is placed on the placing portion. The second member 1120 is inserted into the first member 1110 by being moved in a direction approaching each other in the axial direction X with a jig, thereby realizing the assembling. Specifically, first, the second cylindrical portion 1221 of the second member 1220 abuts against the inclined surface 10215 of the claw portion 1214 of the elastic deformation portion 1213 of the first member 1210, then, the axial tip end portion of the elastic deformation portion 1213 is bent outward in the radial direction and deformed, thereafter, the axial tip end portion of the elastic deformation portion 1213 is returned radially inward when the claw portion 1214 of the elastic deformation portion 1213 reaches the groove portion 1223 of the second member 1220, and the claw portion 1214 is hooked to the groove portion 1223. Incidentally, the assembling of the second member 1220 to the first member 1210 described above may be performed by inserting the second member 1220 from above the first member 1210 in a state in which the first member 1210 is set with the axial end portion thereof on the placing portion 1212 side positioned below.

When the movement is performed and the claw portion 1214 of the elastic deformation portion 1213 of the first member 1210 is hooked by the groove portion 1223 of the second member 1220, the relative movement of the two members 1210, 1220 in the axial direction X by which the two members 1210, 1220 are separated from each other is restricted, and the two members 1210, 1220 are mounted to each other, so that the assembling of the two members 1210, 1220 is completed. When the assembling of the two members 1210, 1220 is completed, the placing portion 1212 and the facing portion 1222 sandwich the culture membrane 1010 (specifically, the support frame 1012) therebetween, and the claw portion 1214 of the first member 1210 is locked to the groove portion 1223 of the second member 1220.

According to the structure of the cell culture device 1200, after the first member 1210 and the second member 1220 are assembled, the relative movement between the first member 1210 and the second member 1220 in the axial direction X can be restricted by the elastic deformation portion 1213 and the groove portion 1223 as the locking portions in a state in which the support frame 1012 of the culture membrane 1010 is sandwiched between the first member 1210 and the second member 1220. Therefore, adhesiveness in the assembled state of the first member 1210 and the second member 1220 sandwiching the culture membrane 1010 can be improved, and a sealing property on both sides sandwiching the culture membrane 1010 during the cell culture can be ensured.

After the assembling of the first member 1210 and the second member 1220 is completed as described above, the cell culture is performed on both surfaces of the culture membrane 1010 in the same manner as in the third embodiment. Therefore, according to the cell culture device 1200, the same effects as those of the cell culture device 1001 of the third embodiment can be obtained. In addition, according to the cell culture device 1200, since the assembling of the first member 1210 and the second member 1220 can be realized only by moving the two members 1210, 1220 in the axial direction X, assemblability can be simplified and an assembling work can be facilitated.

In order to release the assembling of the first member 1210 and the second member 1220, as shown in FIG. 18, the elastic deformation portion 1213 of the first member 1210 may be forcibly bent outward in the radial direction and deformed using a rod-shaped jig 1300, and in this state, the second member 1220 may be pulled out in the axial direction X from the first member 1210. In addition, in order to release the assembling of the first member 1210 and the second member 1220 using the jig 1300, a part of the inclined surface 1215 needs to be positioned radially outward of the outer surface of the second cylindrical portion 1221 of the second member 1220 so that the jig 1300 can abut against the inclined surface 1215 of the claw portion 1214, in a state in which the claw portion 1214 of the elastic deformation portion 1213 of the first member 1210 is hooked by the groove portion 1223 of the second member 1220. According to this configuration, the assembling of the first member 1210 and the second member 1220 can be released using the jig 1300.

In the fifth embodiment, the elastic deformation portion 1213 of the first member 1210 and the groove portion 1223 of the second member 1220 each correspond to the "locking portion" described in the claims.

In the fifth embodiment, the first member 1210 includes the elastic deformation portion 1213 provided with the claw portion 1214 protruding radially inward from the plate-shaped main body, and the second member 1220 includes the groove portion 1223 provided on the outer surface of the second cylindrical portion 1221 so as to be recessed radially inward. However, the present invention is not limited to this, and the first member 1210 may have a groove portion provided on the inner surface of the first cylindrical portion 1211 so as to be recessed radially outward, and the second member 1220 may have an elastic deformation portion provided with a claw portion protruding radially outward from the plate-shaped main body.

In the third, fourth, and fifth embodiments described above, the culture membrane 1010 includes the membrane body 1011 and the annular support frame 1012 joined to the peripheral edge of the membrane body 1011. However, the present invention is not limited to this, and the support frame 1012 may be formed in, for example, a cross shape or a net shape when viewed from the axial direction X as long as the support frame 1012 has a frame-like structure joined to the membrane body 1011.

The present invention is not limited to the above-described embodiments and modifications, and various changes can be made without departing from the spirit of the present invention.

According to an aspect of the invention, there is provided a cell culture device comprising: a holding member including a main body cylindrical portion extending in a cylindrical shape in an axial direction and a holding portion provided at an axially intermediate portion of the main body cylindrical portion and holding a culture membrane; a first cylindrical member detachably mounted on one axial side with respect to the holding member, extending in a cylindrical shape in the axial direction, and protruding from one axial end of the holding member toward the one axial side when being mounted to the holding member; and a second cylindrical member detachably mounted on another axial side with respect to the holding member, extending in a cylindrical shape in the axial direction, and protruding from another axial end of the holding member toward the other axial side when being mounted to the holding member.

According to this configuration, when two types of cells are seeded on both surfaces of the culture membrane, the cell culture device can be used in a state of removing either of the first cylindrical member and the second cylindrical member which is positioned on a lower side of the holding member from the holding member without requiring both the first cylindrical member and the second cylindrical member to be mounted to the holding member and them to be used at the same time. In addition, the first cylindrical member protrudes from one axial end of the holding member toward the one axial side in a state of being engaged with and fixed to the holding member, and the second cylindrical member protrudes from the other axial end of the holding member toward the other axial side in a state of being engaged with and fixed to the holding member. Therefore, according to the cell culture device, since a dimensional distance from an axial lower end to the holding portion holding the culture membrane can be shortened when the cell culture is performed, cells can be cultured on the culture membrane with a small amount of culture solution.

According to an aspect of the invention, there is also provided a cell culture device comprising: a culture membrane including a membrane body and a support frame joined to the membrane body; a first member including a first cylindrical portion extending in a cylindrical shape in an axial direction and a placing portion which is formed with an axial end surface facing in the axial direction, which is configured to abut against the support frame, and on which the culture membrane is placed; and a second member including a second cylindrical portion extending in a cylindrical shape in the axial direction and a facing portion which faces the axial end surface of the placing portion in the axial direction, the facing portion and the placing portion sandwiching the support frame therebetween, wherein the first member and the second member each have a locking portion which is configured to restrict a relative movement between the first member and the second member in the axial direction by which the first member and the second member are separated from each other in a state in which the placing portion and the facing portion are assembled to each other so as to sandwich the support frame therebetween.

According to this configuration, the locking portion can restrict a relative movement between the first member and the second member in the axial direction by which the first member and the second member are separated from each other in a state in which the placing portion of the first member and the facing portion of the second member are assembled to each other so as to sandwich the support frame of the culture membrane therebetween. Therefore, adhesiveness in the assembled state between the first member and the second member sandwiching the culture membrane can be improved, and a sealing properly between on both sides sandwiching the culture membrane during cell culture can be ensured.

What is claimed is:

1. A cell culture device comprising:
   a culture membrane including a membrane body and a support frame joined to the membrane body;
   a first member including a first cylindrical portion extending in a cylindrical shape in an axial direction and a placing portion which is formed with an axial end surface facing in the axial direction, which is configured to abut against the support frame, and on which the culture membrane is placed; and
   a second member including a second cylindrical portion extending in a cylindrical shape in the axial direction and a facing portion which faces the axial end surface of the placing portion in the axial direction, the facing portion and the placing portion sandwiching the support frame therebetween, wherein
   the first member and the second member each have a locking portion which is configured to restrict a relative movement between the first member and the second member in the axial direction by which the first member and the second member are separated from each other in a state in which the placing portion and the facing portion are assembled to each other so as to sandwich the support frame therebetween, wherein
   the first member includes a side surface opening portion which is provided so as to penetrate, in a radial direction, a predetermined portion of a peripheral wall of the first cylindrical portion including at least a part of a placing surface, on which the culture membrane is placed, of the placing portion, and which opens a part of the first cylindrical portion.

2. The cell culture device according to claim 1, wherein the locking portion includes
   a concave portion which is provided in one of the first cylindrical portion and the second cylindrical portion and extends in a peripheral direction, and
   a convex portion which is provided on the other of the first cylindrical portion and the second cylindrical portion, and which is configured to relatively move in the concave portion and fit into the concave portion by a relative rotation of the first member and the second member in the peripheral direction.

3. The cell culture device according to claim 2, wherein the concave portion is provided on a peripheral wall on the one of the first cylindrical portion and the second cylindrical portion so as to be recessed in a radial direction, and the convex portion is provided on a peripheral wall on the other one of the first cylindrical portion and the second cylindrical portion so as to protrude in the radial direction.

4. The cell culture device according to claim 1, wherein the locking portion includes an elastic deformation portion which is provided on one of the first cylindrical portion and the second cylindrical portion, which is provided with a claw portion protruding radially at an axial tip end portion, and which is elastically deformable in a radial direction, and a groove portion which is provided on the other of the first cylindrical portion and the second cylindrical portion, and to which the claw portion is hooked when the first member and the second member approach each other in the axial direction to a predetermined positional relationship.

5. The cell culture device according to claim 1, wherein the first cylindrical portion includes a peripheral wall portion whose inner peripheral surface is formed so as to be able to guide the culture membrane to the placing portion, and the peripheral wall portion includes a cutout portion penetrating in a radial direction and extending in the axial direction from an axial end portion of the first cylindrical portion toward a portion where the placing portion is provided.

6. The cell culture device according to claim 1, wherein the first cylindrical portion includes a peripheral wall portion whose inner peripheral surface is formed so as to be able to guide the culture membrane to the placing portion, the peripheral wall portion includes a cutout portion penetrating in a radial direction and extending in the axial direction from an axial end portion of the first cylindrical portion toward a portion where the placing portion is provided, and the side surface opening portion and the cutout portion are provided at the same position in a peripheral direction on the first member and are arranged so as to be continuous with each other in the axial direction.

7. The cell culture device according to claim 1, wherein the first cylindrical portion includes a peripheral wall portion whose inner peripheral surface is formed so as to be able to guide the culture membrane to the placing portion, the peripheral wall portion includes a cutout portion penetrating in a radial direction and extending in the axial direction from an axial end portion of the first cylindrical portion toward a portion where the placing portion is provided, and the side surface opening portion and the cutout portion are provided at different positions in a peripheral direction on the first member.

* * * * *